(12) United States Patent
Mullen et al.

(10) Patent No.: US 8,668,143 B2
(45) Date of Patent: *Mar. 11, 2014

(54) PAYMENT CARDS AND DEVICES WITH GIFT CARD, GLOBAL INTEGRATION, AND MAGNETIC STRIPE READER COMMUNICATION FUNCTIONALITY

(75) Inventors: Jeffrey D. Mullen, Pittsburgh, PA (US); David Lambeth, Pittsburgh, PA (US); Bruce Cloutier, Jeannette, PA (US)

(73) Assignee: Dynamics Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/186,553

(22) Filed: Jul. 20, 2011

(65) Prior Publication Data
US 2011/0276436 A1 Nov. 10, 2011

Related U.S. Application Data

(63) Continuation of application No. 12/339,051, filed on Dec. 19, 2008.

(60) Provisional application No. 61/016,491, filed on Dec. 24, 2007, provisional application No. 61/026,846, filed on Feb. 7, 2008, provisional application No. 61/027,807, filed on Feb. 11, 2008, provisional application No. 61/081,003, filed on Jul. 15, 2008, provisional application No. 61/086,239, filed on Aug. 5, 2008, provisional application No. 61/090,423, filed on Aug. 20, 2008, provisional application No. 61/097,401, filed on Sep. 16, 2008, provisional application No. 61/112,766, filed on Nov. 9, 2008, provisional application No. 61/117,186, filed on Nov. 23, 2008, provisional application No. 61/119,366, filed on Dec. 2, 2008, provisional application No. 61/120,813, filed on Dec. 8, 2008.

(51) Int. Cl.
*G06K 5/00* (2006.01)

(52) U.S. Cl.
USPC ........... 235/380; 235/441; 235/451; 235/492; 235/487

(58) Field of Classification Search
USPC .......... 379/93.17; 705/39; 235/380, 441, 451, 235/492, 487
See application file for complete search history.

(56) References Cited

U.S. PATENT DOCUMENTS

| | | |
|---|---|---|
| 4,353,064 A | 10/1982 | Stamm |
| 4,394,654 A | 7/1983 | Hofmann-Cerfontaine |

(Continued)

FOREIGN PATENT DOCUMENTS

| | | |
|---|---|---|
| EP | 0203683 | 12/1986 |
| GB | 2420098 | 5/2006 |

(Continued)

OTHER PUBLICATIONS

U.S. Appl. No. 60/594,300, Poidomani et al.

(Continued)

*Primary Examiner* — Sonji Johnson

(57) ABSTRACT

A payment card (e.g., credit and/or debit card) or other device (e.g., mobile telephone) is provided with a magnetic emulator operable to communicate data to a magnetic stripe read-head. Gift cards may be inputted by a user into such a payment card or other device such that a user can combine gift cards. Similarly, a user be provided with a global payment account that can be utilized in multiple countries that have different standards for formatting data. A user may be provided with a default country (e.g., United States) but may have a way to select that the user is in a different country (e.g., Japan). Accordingly, a user may select that a Japanese data structure be transmitted through a magnetic stripe reader when the user is in Japan.

20 Claims, 17 Drawing Sheets

(56) References Cited

U.S. PATENT DOCUMENTS

| | | |
|---|---|---|
| 4,614,861 A | 9/1986 | Pavlov et al. |
| 4,667,087 A | 5/1987 | Quintana |
| 4,701,601 A | 10/1987 | Francini et al. |
| 4,720,860 A | 1/1988 | Weiss |
| 4,786,791 A | 11/1988 | Hodama |
| 4,791,283 A | 12/1988 | Burkhardt |
| 4,797,542 A | 1/1989 | Hara |
| 5,038,251 A | 8/1991 | Sugiyama et al. |
| 5,168,520 A | 12/1992 | Weiss |
| 5,237,614 A | 8/1993 | Weiss |
| 5,276,311 A | 1/1994 | Hennige |
| 5,347,580 A | 9/1994 | Molva et al. |
| 5,361,062 A | 11/1994 | Weiss et al. |
| 5,412,199 A | 5/1995 | Finkelstein et al. |
| 5,434,398 A | 7/1995 | Goldberg |
| 5,434,405 A | 7/1995 | Finkelstein et al. |
| 5,478,994 A | 12/1995 | Rahman |
| 5,479,512 A | 12/1995 | Weiss |
| 5,484,997 A | 1/1996 | Haynes |
| 5,485,519 A | 1/1996 | Weiss |
| 5,585,787 A | 12/1996 | Wallerstein |
| 5,591,949 A | 1/1997 | Bernstein |
| 5,608,203 A | 3/1997 | Finkelstein et al. |
| 5,623,552 A | 4/1997 | Lane |
| 5,657,388 A | 8/1997 | Weiss |
| 5,834,747 A | 11/1998 | Cooper |
| 5,834,756 A | 11/1998 | Gutman et al. |
| 5,856,661 A | 1/1999 | Finkelstein et al. |
| 5,864,623 A | 1/1999 | Messina et al. |
| 5,907,142 A | 5/1999 | Kelsey |
| 5,913,203 A | 6/1999 | Wong et al. |
| 5,937,394 A | 8/1999 | Wong et al. |
| 5,955,021 A | 9/1999 | Tiffany, III |
| 5,955,961 A | 9/1999 | Wallerstein |
| 5,956,699 A | 9/1999 | Wong et al. |
| 6,025,054 A | 2/2000 | Tiffany, III |
| 6,045,043 A | 4/2000 | Bashan et al. |
| 6,076,163 A | 6/2000 | Hoffstein et al. |
| 6,085,320 A | 7/2000 | Kaliski |
| 6,095,416 A | 8/2000 | Grant et al. |
| 6,130,621 A | 10/2000 | Weiss |
| 6,145,079 A | 11/2000 | Mitty et al. |
| 6,157,920 A | 12/2000 | Jakobsson et al. |
| 6,161,181 A | 12/2000 | Haynes, III et al. |
| 6,176,430 B1 | 1/2001 | Finkelstein et al. |
| 6,182,894 B1 | 2/2001 | Hackett et al. |
| 6,189,098 B1 | 2/2001 | Kaliski |
| 6,199,052 B1 | 3/2001 | Mitty et al. |
| 6,206,293 B1 | 3/2001 | Gutman et al. |
| 6,240,184 B1 | 5/2001 | Huynh et al. |
| 6,241,153 B1 | 6/2001 | Tiffany, III |
| 6,256,873 B1 | 7/2001 | Tiffany, III |
| 6,269,163 B1 | 7/2001 | Rivest et al. |
| 6,286,022 B1 | 9/2001 | Kaliski et al. |
| 6,308,890 B1 | 10/2001 | Cooper |
| 6,313,724 B1 | 11/2001 | Osterweil |
| 6,389,442 B1 | 5/2002 | Yin et al. |
| 6,393,447 B1 | 5/2002 | Jakobsson et al. |
| 6,411,715 B1 | 6/2002 | Liskov et al. |
| 6,446,052 B1 | 9/2002 | Juels |
| 6,460,141 B1 | 10/2002 | Olden |
| 6,592,044 B1 | 7/2003 | Wong et al. |
| 6,607,127 B2 | 8/2003 | Wong |
| 6,609,654 B1 | 8/2003 | Anderson et al. |
| 6,631,849 B2 | 10/2003 | Blossom |
| 6,655,585 B2 | 12/2003 | Shinn |
| 6,681,988 B2 | 1/2004 | Stack et al. |
| 6,705,520 B1 | 3/2004 | Pitroda et al. |
| 6,755,341 B1 | 6/2004 | Wong et al. |
| 6,764,005 B2 | 7/2004 | Cooper |
| 6,769,618 B1 | 8/2004 | Finkelstein |
| 6,805,288 B2 | 10/2004 | Routhenstein et al. |
| 6,811,082 B2 | 11/2004 | Wong |
| 6,813,354 B1 | 11/2004 | Jakobsson et al. |
| 6,817,532 B2 | 11/2004 | Finkelstein |
| 6,873,974 B1 | 3/2005 | Schutzer |
| 6,902,116 B2 | 6/2005 | Finkelstein |
| 6,970,070 B2 | 11/2005 | Juels et al. |
| 6,980,969 B1 | 12/2005 | Tuchler et al. |
| 6,985,583 B1 | 1/2006 | Brainard et al. |
| 6,991,155 B2 | 1/2006 | Burchette, Jr. |
| 7,013,030 B2 | 3/2006 | Wong et al. |
| 7,035,443 B2 | 4/2006 | Wong |
| 7,039,223 B2 | 5/2006 | Wong |
| 7,044,394 B2 | 5/2006 | Brown |
| 7,051,929 B2 | 5/2006 | Li |
| 7,066,386 B2 | 6/2006 | Izumi |
| 7,083,094 B2 | 8/2006 | Cooper |
| 7,100,049 B2 | 8/2006 | Gasparini et al. |
| 7,100,821 B2 | 9/2006 | Rasti |
| 7,111,172 B1 | 9/2006 | Duane et al. |
| 7,114,652 B2 | 10/2006 | Moullette et al. |
| 7,136,514 B1 | 11/2006 | Wong |
| 7,140,550 B2 | 11/2006 | Ramachandran |
| 7,163,153 B2 | 1/2007 | Blossom |
| 7,195,154 B2 | 3/2007 | Routhenstein |
| 7,197,639 B1 | 3/2007 | Juels et al. |
| 7,219,368 B2 | 5/2007 | Juels et al. |
| 7,225,537 B2 | 6/2007 | Reed |
| 7,225,994 B2 | 6/2007 | Finkelstein |
| 7,246,752 B2 | 7/2007 | Brown |
| 7,298,243 B2 | 11/2007 | Juels et al. |
| 7,334,732 B2 | 2/2008 | Cooper |
| 7,337,326 B2 | 2/2008 | Palmer et al. |
| 7,346,775 B2 | 3/2008 | Gasparini et al. |
| 7,347,376 B1 * | 3/2008 | Biss et al. ............... 235/472.01 |
| 7,356,696 B1 | 4/2008 | Jakobsson et al. |
| 7,357,319 B1 | 4/2008 | Lin et al. |
| 7,359,507 B2 | 4/2008 | Kaliski |
| 7,360,688 B1 | 4/2008 | Harris |
| 7,363,494 B2 | 4/2008 | Brainard et al. |
| 7,380,710 B2 | 6/2008 | Brown |
| 7,398,253 B1 | 7/2008 | Pinnell |
| 7,404,087 B2 | 7/2008 | Teunen |
| 7,424,570 B2 | 9/2008 | D'Albore et al. |
| 7,427,033 B1 | 9/2008 | Roskind |
| 7,454,349 B2 | 11/2008 | Teunen et al. |
| 7,461,250 B1 | 12/2008 | Duane et al. |
| 7,461,399 B2 | 12/2008 | Juels et al. |
| 7,472,093 B2 | 12/2008 | Juels |
| 7,472,829 B2 | 1/2009 | Brown |
| 7,494,055 B2 | 2/2009 | Fernandes et al. |
| 7,502,467 B2 | 3/2009 | Brainard et al. |
| 7,502,933 B2 | 3/2009 | Jakobsson et al. |
| 7,503,485 B1 | 3/2009 | Routhenstein |
| 7,516,492 B1 | 4/2009 | Nisbet et al. |
| 7,523,301 B2 | 4/2009 | Nisbet et al. |
| 7,530,495 B2 | 5/2009 | Cooper |
| 7,532,104 B2 | 5/2009 | Juels |
| 7,543,739 B2 | 6/2009 | Brown et al. |
| 7,559,464 B2 | 7/2009 | Routhenstein |
| 7,562,221 B2 | 7/2009 | Nystrom et al. |
| 7,562,222 B2 | 7/2009 | Gasparini et al. |
| 7,580,898 B2 | 8/2009 | Brown et al. |
| 7,584,153 B2 | 9/2009 | Brown et al. |
| 7,591,426 B2 | 9/2009 | Osterweil et al. |
| 7,591,427 B2 | 9/2009 | Osterweil |
| 7,594,611 B1 | 9/2009 | Arrington, III |
| 7,602,904 B2 | 10/2009 | Juels et al. |
| 7,631,804 B2 | 12/2009 | Brown |
| 7,639,537 B2 | 12/2009 | Sepe et al. |
| 7,641,124 B2 | 1/2010 | Brown et al. |
| 7,660,902 B2 | 2/2010 | Graham et al. |
| 7,729,984 B1 | 6/2010 | Nappi |
| 7,828,207 B2 | 11/2010 | Cooper |
| 7,908,216 B1 | 3/2011 | Davis et al. |
| 8,004,514 B2 * | 8/2011 | Sampsell ............... 345/212 |
| 2001/0034702 A1 | 10/2001 | Mockett |
| 2001/0047335 A1 | 11/2001 | Arndt et al. |
| 2002/0043566 A1 | 4/2002 | Goodman et al. |
| 2002/0059114 A1 | 5/2002 | Cockrill et al. |
| 2002/0082989 A1 | 6/2002 | Fife et al. |
| 2002/0096570 A1 | 7/2002 | Wong et al. |
| 2002/0099607 A1 | 7/2002 | Sosa et al. |

(56) References Cited

U.S. PATENT DOCUMENTS

| | | |
|---|---|---|
| 2002/0120583 A1 | 8/2002 | Keresman, III et al. |
| 2003/0021398 A1* | 1/2003 | Donnelly et al. .......... 379/93.17 |
| 2003/0034388 A1 | 2/2003 | Routhenstein et al. |
| 2003/0052168 A1 | 3/2003 | Wong |
| 2003/0057278 A1 | 3/2003 | Wong |
| 2003/0116635 A1 | 6/2003 | Taban |
| 2003/0152253 A1 | 8/2003 | Wong |
| 2003/0163287 A1 | 8/2003 | Vock et al. |
| 2003/0173409 A1 | 9/2003 | Vogt et al. |
| 2003/0179909 A1 | 9/2003 | Wong et al. |
| 2003/0179910 A1 | 9/2003 | Wong |
| 2003/0226899 A1 | 12/2003 | Finkelstein |
| 2004/0035942 A1 | 2/2004 | Silverman |
| 2004/0133787 A1 | 7/2004 | Doughty |
| 2004/0162732 A1 | 8/2004 | Rahim et al. |
| 2004/0172535 A1 | 9/2004 | Jakobsson |
| 2004/0177045 A1 | 9/2004 | Brown |
| 2005/0043997 A1 | 2/2005 | Sahota et al. |
| 2005/0065884 A1 | 3/2005 | Capurso et al. |
| 2005/0080747 A1 | 4/2005 | Anderson et al. |
| 2005/0086160 A1 | 4/2005 | Wong et al. |
| 2005/0086177 A1 | 4/2005 | Anderson et al. |
| 2005/0116026 A1 | 6/2005 | Burger et al. |
| 2005/0119940 A1 | 6/2005 | Concilio et al. |
| 2005/0154643 A1 | 7/2005 | Doan et al. |
| 2005/0211767 A1 | 9/2005 | Sawachi |
| 2005/0228959 A1 | 10/2005 | D'Albore et al. |
| 2005/0246292 A1* | 11/2005 | Sarcanin .......... 705/67 |
| 2006/0000900 A1 | 1/2006 | Fernandes et al. |
| 2006/0037073 A1 | 2/2006 | Juels et al. |
| 2006/0041759 A1 | 2/2006 | Kaliski et al. |
| 2006/0085328 A1 | 4/2006 | Cohen et al. |
| 2006/0091223 A1 | 5/2006 | Zellner |
| 2006/0161435 A1 | 7/2006 | Atef et al. |
| 2006/0163353 A1 | 7/2006 | Moulette et al. |
| 2006/0174104 A1 | 8/2006 | Crichton et al. |
| 2006/0186212 A1 | 8/2006 | Cooper |
| 2006/0196929 A1 | 9/2006 | Kelley et al. |
| 2006/0196931 A1 | 9/2006 | Holtmanns et al. |
| 2006/0256961 A1 | 11/2006 | Brainard et al. |
| 2007/0034700 A1 | 2/2007 | Poidomani et al. |
| 2007/0114274 A1 | 5/2007 | Gibbs et al. |
| 2007/0124321 A1 | 5/2007 | Szydlo |
| 2007/0131759 A1 | 6/2007 | Cox et al. |
| 2007/0138299 A1 | 6/2007 | Mitra |
| 2007/0139299 A1 | 6/2007 | Huang et al. |
| 2007/0152070 A1 | 7/2007 | D'Albore |
| 2007/0152072 A1 | 7/2007 | Frallicciardi et al. |
| 2007/0153487 A1 | 7/2007 | Frallicciardi et al. |
| 2007/0174614 A1 | 7/2007 | Duane et al. |
| 2007/0192245 A1* | 8/2007 | Fisher et al. .......... 705/39 |
| 2007/0192249 A1 | 8/2007 | Biffle et al. |
| 2007/0208671 A1 | 9/2007 | Brown et al. |
| 2007/0241183 A1 | 10/2007 | Brown et al. |
| 2007/0241201 A1 | 10/2007 | Brown et al. |
| 2007/0242008 A1 | 10/2007 | Cummings |
| 2007/0256123 A1 | 11/2007 | Duane et al. |
| 2007/0291753 A1 | 12/2007 | Romano |
| 2008/0005510 A1 | 1/2008 | Sepe et al. |
| 2008/0008315 A1 | 1/2008 | Fontana et al. |
| 2008/0008322 A1 | 1/2008 | Fontana et al. |
| 2008/0010675 A1 | 1/2008 | Massascusa et al. |
| 2008/0016351 A1 | 1/2008 | Fontana et al. |
| 2008/0019507 A1 | 1/2008 | Fontana et al. |
| 2008/0028447 A1 | 1/2008 | O'Malley et al. |
| 2008/0040271 A1 | 2/2008 | Hammad et al. |
| 2008/0040276 A1 | 2/2008 | Hammad et al. |
| 2008/0058016 A1 | 3/2008 | Di Maggio et al. |
| 2008/0059379 A1 | 3/2008 | Ramaci et al. |
| 2008/0067247 A1 | 3/2008 | McGregor et al. |
| 2008/0096326 A1 | 4/2008 | Reed |
| 2008/0116285 A1 | 5/2008 | Shoemaker |
| 2008/0126398 A1 | 5/2008 | Cimino |
| 2008/0128515 A1 | 6/2008 | Di Iorio |
| 2008/0148394 A1 | 6/2008 | Poidomani et al. |
| 2008/0201264 A1 | 8/2008 | Brown et al. |
| 2008/0209550 A1 | 8/2008 | Di Iorio |
| 2008/0288699 A1 | 11/2008 | Chichierchia |
| 2008/0294930 A1 | 11/2008 | Varone et al. |
| 2008/0302877 A1 | 12/2008 | Musella et al. |
| 2008/0319912 A1 | 12/2008 | Faith et al. |
| 2009/0013122 A1 | 1/2009 | Sepe et al. |
| 2009/0036147 A1 | 2/2009 | Romano |
| 2009/0037275 A1 | 2/2009 | Pollio |
| 2009/0046522 A1 | 2/2009 | Sepe et al. |
| 2009/0078777 A1 | 3/2009 | Granucci et al. |
| 2009/0081990 A1 | 3/2009 | Granucci et al. |
| 2009/0108064 A1 | 4/2009 | Fernandes et al. |
| 2009/0150295 A1 | 6/2009 | Hatch et al. |
| 2009/0152365 A1 | 6/2009 | Li et al. |
| 2009/0240625 A1 | 9/2009 | Faith et al. |
| 2009/0242648 A1 | 10/2009 | Di Sirio et al. |
| 2009/0244858 A1 | 10/2009 | Di Sirio et al. |
| 2009/0253460 A1 | 10/2009 | Varone et al. |
| 2009/0255996 A1 | 10/2009 | Brown et al. |
| 2009/0290704 A1 | 11/2009 | Cimino |
| 2009/0303885 A1 | 12/2009 | Longo |
| 2011/0028184 A1 | 2/2011 | Cooper |

FOREIGN PATENT DOCUMENTS

| | | |
|---|---|---|
| JP | 05210770 A | 8/1993 |
| WO | WO9852735 | 11/1998 |
| WO | WO0247019 | 6/2002 |
| WO | WO2006066322 | 6/2006 |
| WO | WO2006080929 | 8/2006 |
| WO | WO2006105092 | 10/2006 |
| WO | WO2006116772 | 11/2006 |
| WO | WO2007141779 | 12/2007 |
| WO | WO2008064403 | 6/2008 |

OTHER PUBLICATIONS

U.S. Appl. No. 60/675,388, Poidomani et al.
The Bank Credit Card Business. Second Edition, American Bankers Association, Washington, D.C., 1996.
A Day in the Life of a Flux Reversal. http://www.phrack.org/issues.html?issue=37&id=6#article. As viewed on Apr. 12, 2010.
Dynamic Virtual Credit Card Numbers. http://homes.cerias.purdue.edu/~jtli/paper/fc07.pdf. As viewed on Apr. 12, 2010.
USPTO, International Search Report, Apr. 28, 2009.
English translation of JP 05210770 A.
EPO, Extended European Search Report, Jan. 26, 2012.
AU, Patent Examination Report No. 1, Oct. 11, 2012.

* cited by examiner

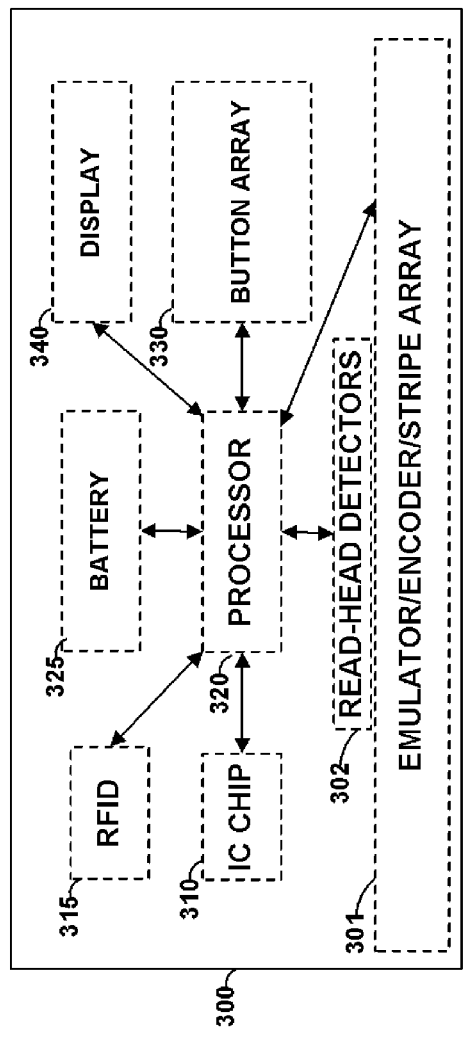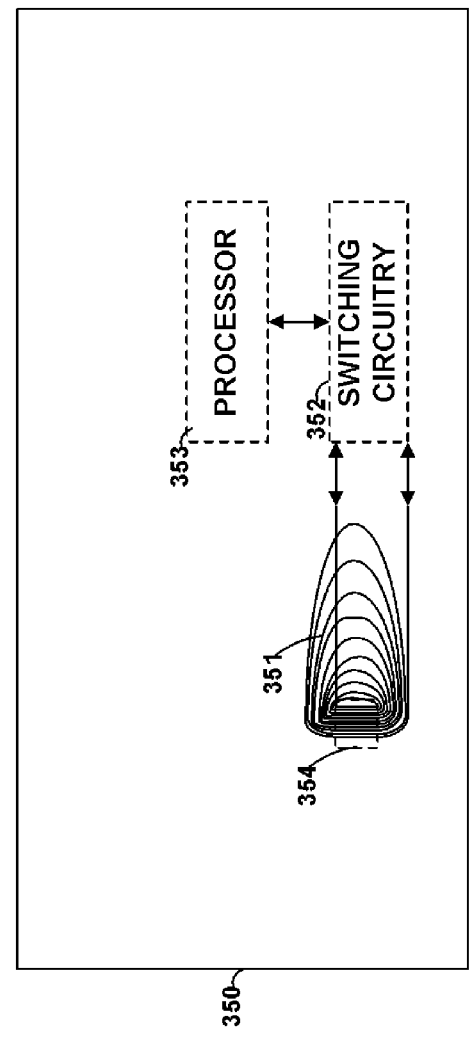
FIG. 3

PAYMENT CARDS AND DEVICES WITH GIFT CARD, GLOBAL INTEGRATION, AND MAGNETIC STRIPE READER COMMUNICATION FUNCTIONALITY

CROSS-REFERENCE TO RELATED APPLICATIONS

This application is a continuation of U.S. patent application Ser. No. 12/339,051, filed on Dec. 19, 2008, which claims the benefit of U.S. Provisional Patent Application Nos. 61/016,491 filed on Dec. 24, 2007, 61/026,846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008, 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to magnetic cards and payment systems.

SUMMARY OF THE INVENTION

A card is provided, such as a credit card or security card, that may transmit information to a magnetic stripe reader via a magnetic emulator. The magnetic emulator may be, for example, a circuit that emits electromagnetic fields operable to electrically couple with a read-head of a magnetic stripe reader such that data may be transmitted from the circuit to the magnetic stripe reader. The emulator may be operated serially such that information is transmitted serially to a magnetic stripe reader. Alternatively, for example, portions of a magnetic emulator may emit different electromagnetic fields at a particular instance such that the emulator is operated to provide physically parallel, instantaneous data. Alternatively still, a magnetic medium may be provided and a circuit may be provided to change the magnetic properties of the magnetic medium such that a magnetic stripe reader is operable to read information written on the magnetic medium.

A processor may be provided on a card, or other device, that controls a magnetic emulator. The processor may be configured to operate the emulator such that the emulator transmits serial or parallel information. Particularly, the processor may decouple portions of an emulator from one another such that different portions of the emulator may transmit different information (e.g., transmit data in a parallel operation). The processor may couple portions of an emulator together (or drive the portions together) such that all portions of the emulator transmits the same information (e.g., transmit data in a serial operation). Alternatively, the processor may drive a portion of the emulator to transmit data using one method (e.g., serially) while the processor drives another portion of the emulator using a different method (e.g., in parallel).

The processor may drive an emulator through a switching circuit. The switching circuit may control the direction and magnitude of current that flows through at least a portion of an emulator such that the switching circuit controls the direction and magnitude of the electromagnetic field created by at least that portion of the emulator. An electromagnetic field may be generated by the emulator such that the emulator is operable to electrically couple with a read-head from a magnetic stripe reader without making physical contact with the read-head. Particularly, for example, an emulator that is driven with increased current can be operable to couple with the read-head of a magnetic stripe reader even when placed outside and within the proximity of (e.g., 0.25 inches or more) the read-head.

A processor may detect, for example, the presence of a read-head of a magnetic stripe reader by receiving signals from a magnetic stripe reader detector and, in response, the processor may drive a magnetic emulator in a manner that allows the emulator to couple with the magnetic stripe reader. More than one emulator may be provided on a card or other device and a processor may drive such emulators in a variety of different manners.

A circuit may be provided on a credit card that is operable to receive data from a device, such as a magnetic stripe. In this manner, a card, or other device, may communicate bi-directionally with a device.

An emulator may communicate with a magnetic stripe reader outside of, for example, the housing of a magnetic stripe reader. Accordingly, for example, the emulator may be provided in devices other than cards sized to fit inside of the reading area of a magnetic stripe reader. In other words, for example, the emulator may be located in a device that is thicker than a card—yet the emulator can still communicate with one or more read-heads located in a magnetic stripe reader. Such a device may be, for example, a security token, a wireless communications device, a laptop, a Personal Digital Assistant (PDA), a physical lock key to a house and/or car, or any other device.

Dynamic information may be provided by a processor located on the card, or other device, and communicated through a magnetic emulator. Such dynamic information may, for example, change based on time. For example, the dynamic information may be periodically encrypted differently. One or more displays may be located on a card, or other device, such that the dynamic information may be displayed to a user through the display. Buttons may be provided to accept input from a user to, for example, control the operation of the card or other device.

Dynamic information may include, for example, a dynamic number that is used as, or part of, a number for a credit card number, debit card number, payment card number, and/or payment verification code. Dynamic information may also include, for example, a student identification number or medical identification number. Dynamic information may also, for example, include alphanumeric information such that a dynamic account name is provided.

Read-head detectors may be provided to determine, for example, when a card is being swiped and/or when a read-head is located over a particular portion of a card (e.g., a magnetic emulation circuit). A magnetic emulation circuit may be provided as, for example, a coil. Portions of such a coil may be utilized to detect a read-head while in other portions of the coil may be utilized to communicate information electromagnetically to a read-head. Accordingly, a coil may be utilized to detect a read-head and, after a read-head is detected, the coil may be utilized to, for example, serially transmit information to a magnetic stripe reader.

A read-head detector, or an array of read-head detectors, may be able to, for example, determine the type of reader that the card entered into. For example, a read-head detector array may determine, for example, when a motorized reader was utilized, an insertion reader was utilized, or a user-swipe reader was utilized. Such information may be stored and communicated to a remote storage device (e.g., a remote database). This stored information may be utilized to combat, for example, card cloning. For example, if a particular number of cards (e.g., 10 more) that made consecutive purchases from a machine (e.g., an ATM) detected more than one reader, then, for example, the system may make an autonomous determination that an illegal cloning device was located on front of that ATM machine. If, for example, multiple cards use a restaurant point-of-sale terminal and determine that multiple readers were used then, for example, a computer can make an autonomous determination that cloning may have occurred at the restaurant.

A material may be sandwiched between the two layers to assist in reducing the effect of the electromagnetic fields from one set of coil segments on the side of the material opposite that set of coil segments. Such an interior material may be insulated such that the material does not short the coil segments. Additionally, such an interior material may be chosen, for example, such that the material does not saturate when the coil is conducting current. The coil and material may run, for example, along the location of a track of magnetic data for a payment card. Accordingly, a coil may be fabricated so that the coil wraps around an interior material.

A material may be placed and/or printed on a PCB layer and sandwiched between two other PCB layers. These two other layers may each include coil segments and vias. The middle layer may also include vias such that the material is fabricated to be located in the center of the coil. The material may take a cylindrical, rectangular, square, or any type of shape. Four layers may also be utilized, where the coil segments are printed on a surface of the exterior layers and one or more materials are printed and/or placed on/between the interior layers. A material may be a magnetic material, ferromagnetic material, ferrimagnetic material, or any type of material. For example, copper may be printed on a PCB layer and plated with a material (e.g., nickel, iron, chrome, tin, gold, platinum, cobalt, zinc, allows). A material, for example, may have a relative permeability multiple times greater than the permeability of a vacuum. A material, for example, may have a relative permeability of 2 to 25,000. A material may include, for example, a permalloy, iron, steel, ferrite, nickel or any other material. A material may be an alloy such as a nickel-iron alloy. Such a nickel-iron alloy may include, for example, nickel (e.g., 75-85%), iron, copper, molybdenum and may be placed through one or more annealing processes. Annealing may occur before and/or after the material is placed/printed on a layer of material (e.g., a PCB layer or other layer). A similar and/or different material may be placed either above and/or below a portion, or the entire, set of paths on a layer for a coil. Accordingly, a material may be placed in the interior of a coil as well as along a side of the coil.

Gift cards may be purchased at a store and loaded into a dynamic card. For example, a person may go to a store, purchase a card (at which point the card is activated for use), and give the card to a friend. The friend may then scratch off a removable surface on the gift card to review a dynamic loading code. The friend may utilize user interfaces on the card (e.g., buttons) to load the credit card into the card. Thus, the friend may throw away the gift card but may utilize his/her dynamic card as the gift card. Particularly, the user may utilize a user interface (e.g., a button) on the card to signal to the card that the gift card should be utilized instead of, for example, the user's payment card (e.g., credit card data). Accordingly, the card may communicate the gift card information via a magnetic emulator to a magnetic stripe reader. A processor may provide this information to an RFID antenna located on the card as well as an IC chip located on the card incase, for example, the user utilizes a smartcard or RFID reader located at the point-of-sale.

A user may scratch off a removable surface of a gift card (or other type of card such as a pre-paid payment card) to reveal a code. This code may be entered online at a website that manages the user's payment card (e.g., the user's credit card). The gift card may then attach to the user's credit card. Thus, for example, the user may utilize his/her credit card at a store but the money may be drawn from the gift card. Alternatively, the user may, after making a purchase at a store, go onto his/her payment card's account website and view his/her gift cards. After making a purchase, the user may request a credit refund and may select his/her debit card to be utilized in its place. A period of time may be associated with this. For example, a user may be configured to only be able to utilize gift cards after a purchase for the user's current billing cycle or within a month of purchase.

A user may utilize a user interface on a card or other device (e.g., a mobile telephonic device or other mobile device) to select that a gift card be utilized. The user's payment card information (e.g., debit card information) may be communicated, but the interaction with the user interface may result in additional/different discretionary data being sent from the point-of-sale device through a routing server to an authorization server. One of these servers may look at the discretionary data and may utilize this data to route the information to a different authorization server (e.g., gift card authorization server) or may utilize the information at the authorization server to authorize the information differently (e.g., authorize the gift card purchase). If the amount purchased exceeds the gift card then the payment card may be automatically charged the remaining balance or the cashier may be prompted that the gift card transaction went through at the remaining gift card balance and was applied to the transaction such that the cashier can request additional payment from the customer. Accordingly, a user may enter a simplified code into his/her card order to load his/her payment card with a gift card. For example, a user may enter a code between 16 and 19 digits into a website associated with the user's payment card to attach the gift card to the user's account but may enter a shorter code (e.g., 4-6 characters) into his/her card such that a button is associated with adding/changing discretionary data transmitted by a card (or other data transmitted by a magnetic emulator).

A code that is added to a card may, for example, include data with what button should be utilized activate the transmission of a gift card or other information. Other information may include, for example, the name of a store, the expiration date of the gift card, and the amount of the gift card. For example, a user interface on a card may take the form of a mechanical button. A display may be located next to the button. A code may be entered that causes the display to display "WALMART" everytime the button associated with the display is pressed. Accordingly, a user can see what gift cards are associated with what buttons at any given time. Displays may be, for example, LCD, electronic ink, or any other types of displays. Codes may be generated to delete cards after they are utilized. User interfaces may be associated with deleting gift cards from a user's card.

A global payment card is provided. A global card may, for example, allow a user to utilize the same payment account (e.g., credit account) but may transmit differently structured data depending on the country (e.g., the payment network) the user is located in. For example, suppose Japan includes a nineteen digit payment card number while a U.S. payment card number is fifteen or sixteen digits in length. Accordingly, a user may be provided with a nineteen Japanese number and a sixteen U.S. number when the user is provided with a payment account. The user may be issued with a card that includes a button for Japan. The card may be provided a default such that, for example, a particular country's data structure is utilized by default. Accordingly, a user may utilize the card in the U.S. without changing behavior. However, for example, when the user travels to Japan, the user may interact with a user interface (e.g., a button) such that the Japanese data structure with the Japanese payment information is utilized. Accordingly, a magnetic emulator may be provided to transmit data to a magnetic stripe reader. A processor may also provide the data to an IC chip operable to be read by a smartcard reader and/or an RFID antenna operable to be read by a contactless RFID reader.

Displays may be provided near user interfaces or other structures. For example, a display may be provided next to an LED. Cards may be programmed during manufacturing so that these displays may display particular information. Accordingly, for example, the same card architecture may be utilized to provide a number of different types of cards. A user may utilize user interfaces (e.g., mechanical or capacitive interfaces) to change the function of the display. For example, codes may be entered to reconfigure the displays. Alternatively, for example, a user may utilize buttons to select information to be displayed on displays associated with user interfaces. A code may associate a name of a store with a button and/or a dollar amount. For example, a display may be configured to read "Target $50." Information may be entered manually, but also may be received by a card. For example, a user may swipe a card a second time through a magnetic stripe reader and receive information via a magnetic emulator. This received information may be utilized to update information on the card (e.g., the balance of a gift card, credit account, and/or debit account). Information may also be received by an RFID antenna and/or IC chip located on a card and in communication with a central processor (or distributed processors). For example, transaction information (e.g., list of past transactions, stores where transactions occurred, amounts of transactions) and account information (e.g., balance information, bill information, amount due information) may be communicated to the card and displayed on one or more displays.

A dynamic card may be manufactured in a variety of ways. For example, a dynamic card may be printed onto a flexible material (e.g., a flexible polymer). Multiple layers of this material may be bonded together to form a multiple layer flexible structure. This multiple layer structure may be laminated (e.g., via hot and/or cold lamination) to form a card. The card may be programmed before or after lamination. A card may be programmed via a direct connection between a programmer and one or more contacts on a card. A card may be programmed via a capacitive, optical, or inductive communication via a communication link between a programmer and one or more components (e.g., a contact) on a card. Accordingly, for example, a card may be laminated and capacitively, optically, or inductively programmed. After programming, a processor on the card may be signaled to burn-out its programming communication channel(s) such that no further programming may occur. A portion of the card may not be laminated. Accordingly, a programmer may connect to this non-laminated portion of the card. The non-laminated portion of the card may be laminated after programming. Alternatively, for example, the non-laminated portion of the card may be cut after programming (e.g., and after the processor burns-out its programming ports so the processor cannot be further programmed).

Additional external communication devices may be provided on a card. For example, a USB port or Wi-Fi antenna may be provided on a card. Such additional external communication devices may, for example, allow a user to communicate with stationary computer, laptop, or other device. Such communication devices may, for example, be utilized to load gift cards, or other information (e.g., transactional or account information) from a laptop to a card or other device.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which:

FIG. 3 is an illustration of cards constructed in accordance with the principles of the present invention;

DETAILED DESCRIPTION OF THE INVENTION

Figure 1:
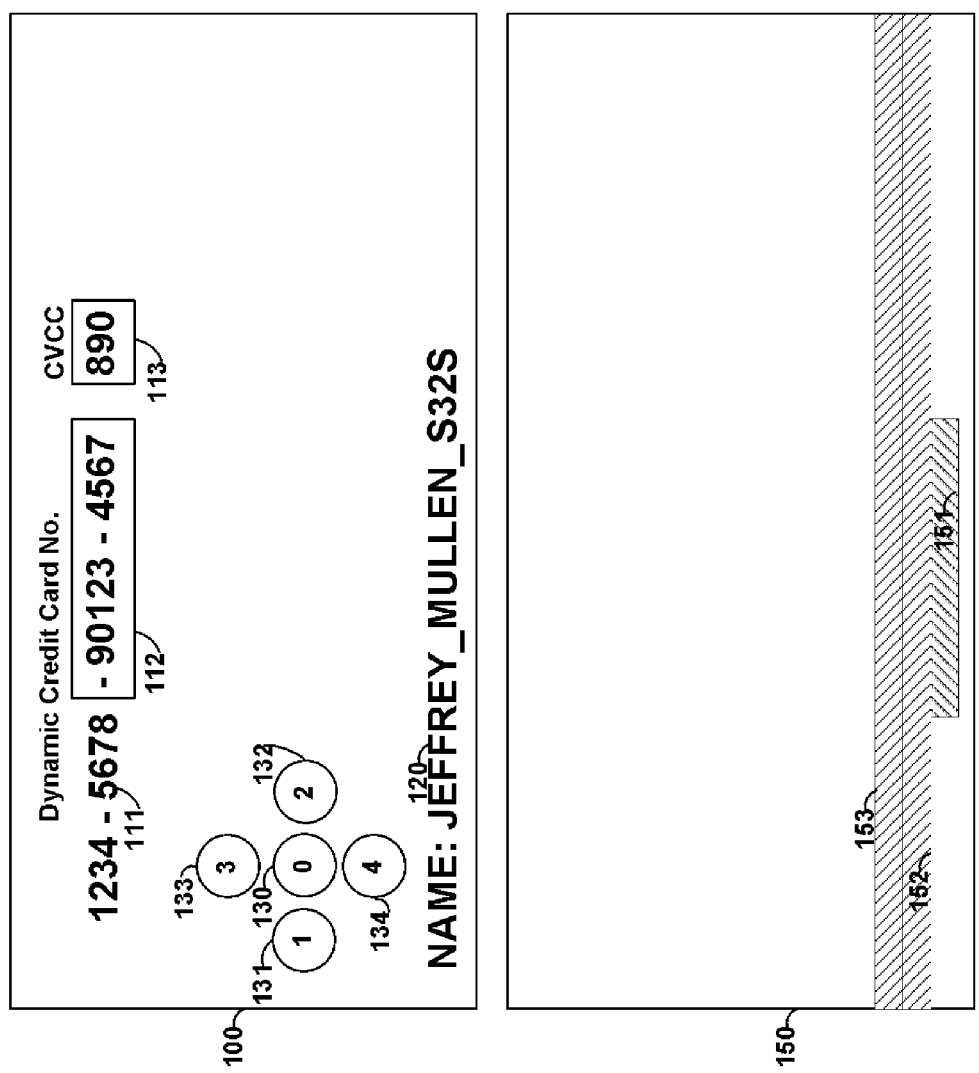
FIG. 1 is an illustration of cards constructed in accordance with the principles of the present invention.

FIG. 1 shows card 100 that includes printed information 111 and 120, displays 112 and 113, and buttons 130-134. Card 100 may be, for example, a payment card such as a credit card, debit card, and/or gift card or any other type of card (e.g., security access or identification card). Payment information, such as a credit/debit card number may be provided as static information 111, dynamic information 112 and/or 113, or any combination thereof.

For example, a particular number of digits of a credit card number (e.g., the last 3 digits) may be provided as dynamic information. Such dynamic information may be changed periodically (e.g., once every hour). Information may be changed via, for example, encryption. Software may be provided at, for example, the payment verification server that verifies the dynamic information for each period of time such that a payment can be validated and processed for a particular user. A user may be identified using, for example, static information that is used to form a credit card number or other static information (e.g., information 120). Additionally, identification information may be derived (e.g., embedded) in dynamic information. Persons skilled in the art will appreciate that a credit card number may have, for example, a length of 15 or 16 digits. A credit card number may also have a length of up to 19 digits. A verification code may be used with some payment systems and such a verification code may be provided statically on the card or may be provided as dynamic information. Such a verification code may be provided on a second display located on, for example, the front or rear surface of card 100. Alternatively, a verification code may be displayed on the same display as other dynamic information (e.g., dynamic information 112). A display may be, for example, a flexible electronic ink display. Such a flexible electronic ink display may, for example, utilize power to change displayed information, but may not utilize power to display information after the information is changed.

Card 150 may be provided. Card 150 may include static magnetic stripe tracks 153 and 152. Magnetic emulator 151 may be included and may be operable to electrically couple with a read-head of a magnetic stripe reader. Persons skilled in the art will appreciate that a read-head housing of a magnetic stripe reader may be provided with one, two, or three active read-heads that are operable to each couple with a separate magnetic track of information. A reader may also have more than one read-head housing and each read-head housing may be provided with one, two, or three active read-heads that are operable to each couple with a separate magnetic track of information. Such read-head housings may be provided different surfaces of a magnetic stripe reader. For example, the read-head housings may be provided on opposite walls of a trough sized to accept payment cards. Accordingly, the devices on the opposite sides of the trough may be able to read a credit card regardless of the direction that the credit card was swiped.

A magnetic emulator may be provided and may be positioned on card 150 such that when card 150 is swiped through a credit card reader, the magnetic emulator passes underneath, or in the proximity of, a read-head for a particular magnetic track. An emulator may be large enough to simultaneously pass beneath, or in the proximity of, multiple read-heads. Information may be transmitted, for example, serially to one or more read-heads. Information from different tracks of data may also be transmitted serially and the magnetic stripe reader may determine the different data received by utilize the starting and/or ending sentinels that define the information for each track. A magnetic emulator may also transmit a string of leading and/or ending zeros such that a magnetic reader may utilize such a string of zeros to provide self-clocking. In doing so, for example, information may be transmitted serially at high speeds to a magnetic stripe reader. For example, credit card information may be transmitted to a magnetic stripe reader at speeds up to, and greater than, 30 Khz).

Different emulators may be provided, and positioned, on card 150 to each couple with a different read-head and each emulator may provide different track information to those different read-heads. Read-head detectors may be utilized to detect when a read-head is over an emulator such that an emulator is controlled by a processor to operate when a read-head detector detects the appropriate presence of a read-head. In doing so, power may be saved. Additionally, the read-head detector may detect how many read-heads are reading the card and, accordingly, only communicate with the associated emulators. In doing so, additional power may be conserved. Accordingly, an emulator may be utilized to communicate dynamic information to a magnetic stripe reader. Such dynamic information may include, for example, dynamic payment card information that changes based on time.

A static magnetic stripe may be provided to transmit data for one or more tracks to a magnetic strip reader where dynamic information is not desired. Card 150, for example, may include static magnetic track 153 and static magnetic track 152. Information on static magnetic tracks 152 and 153 may be encoded via a magnetic stripe encoder. Emulator 151 may be included such that dynamic information may be communicated to a magnetic stripe reader, for example, without a magnetic stripe via an electromagnetic signal transmitted directly from emulator 151 to a read-head of a magnetic stripe reader. Any combination of emulators and static magnetic tracks may be utilized for a card or device (e.g., two magnetic emulators without any magnetic stripes).

One or more batteries, such as flexible lithium polymer batteries, may be utilized to form card 100. Such batteries may be electrically coupled in a serial combination to provide a source of power to the various components of card 100. Alternatively, separate batteries may provide power to different components of card 100. For example, a battery may provide power to a processor and/or display of card 100, while another battery provides a source of energy to one or more magnetic emulators of card 100. In doing so, for example, a processor may operate even after the battery that supplies power to an emulator completely discharges. Accordingly, the processor may provide information to another component of card 100. For example, the processor may display information on a display to indicate to a user that the magnetic emulator is not longer operational due to power exhaustion. Batteries may be, for example, rechargeable and contacts, or other devices, may be provided on card 100 such that the battery may be recharged.

Buttons (e.g., buttons 130-134) may be provided on a card. Such buttons may allow a user to manually provide information to a card. For example, a user may be provided with a personal identification code (e.g., a PIN) and such a personal identification code may be required to be manually inputted into a card using the buttons in order for the card to operate in a particular manner. For example, the use of a magnetic emulator or the use of a display may require a personal identification code.

By dynamically changing a portion of a user's credit card number, for example, credit card fraud is minimized. By allowing the dynamic information to displayed visually to a user, and changed magnetically on a card, user behavior change is minimized (with respect to a credit card with completely static information). By requiring the use of a personal identification code, the fraud associated with lost or stolen credit cards is minimized. Fraud associated with theft/loss is minimized as third party users do not know the personal identification code needed to operate particular aspects of a credit card with dynamic information.

Figure 2:
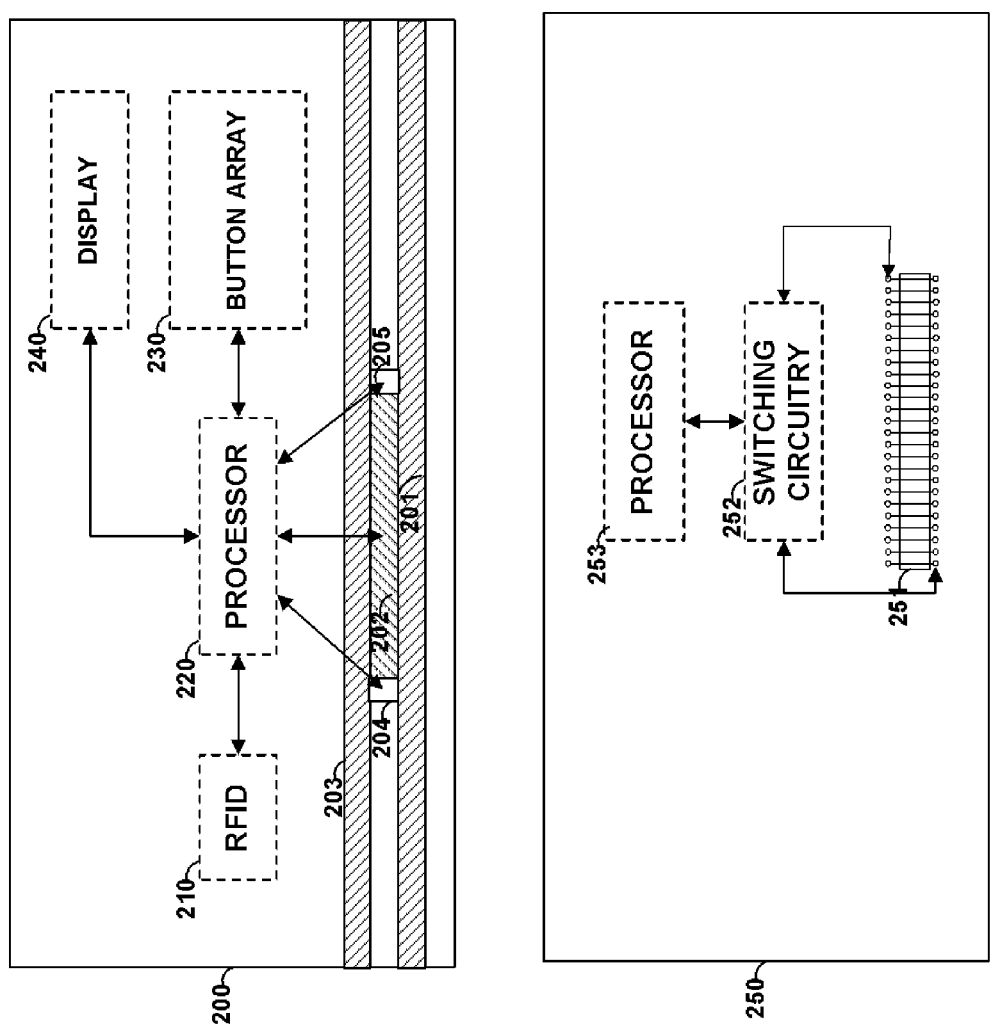
FIG. 2 is an illustration of cards constructed in accordance with the principles of the present invention.

FIG. 2 shows card 200. Card 200 may include, for example, static magnetic stripe track 203, static magnetic stripe track 201, and magnetic emulator 202 sandwiched between read-head detectors 204 and 205. A read-head detector may, for example, be provided as a circuit that detects, for example, changes in capacitance or mechanical coupling to a conductive material. Processor 220 may be provided to, for example, receive information from read-head detectors 204 and 205 and control emulator 202. Persons skilled in the art will appreciate that processor 220 may cause a current to flow through a coil of emulator 202 in a different direction to produce different electromagnetic fields. The transitions between the different electromagnetic fields may be sensed by a magnetic stripe reader as information. Accordingly, a magnetic emulator may transmit data serially while a read-head is electrically coupled with a magnetic reader.

RFID antenna 210 may be provided on card 200. Such an RFID antenna may be operable to transmit information provided by processor 220. In doing so, for example, processor 220 may communicate with an RFID device using RFID antenna 210 and may communicate with a magnetic stripe reader using magnetic emulator 202. Both RFID antenna 210 and magnetic emulator 202 may be utilized to communicate payment card information (e.g., credit card information) to a reader. Processor 240 may also be coupled to display 240 such that dynamic information can be displayed on display 240. Button array 230 may also be coupled to processor 220 such that the operation of card 200 may be controlled, at least in part, by manual input received by button array 230. A smart-card chip may, for example, be included on card 200 in lieu of, or in addition to, RFID 210.

Persons skilled in the art will appreciate that a static magnetic track may be a read-write track such that information may be written to a magnetic track from a magnetic stripe reader that includes a head operable to magnetically encode data onto a magnetic track. Information may be written to a magnetic track as part of a payment process (e.g., a credit card or debit card transaction). Persons skilled in the art will appreciate that a static magnetic track may include a magnetic material that includes ferromagnetic materials that provide for flux-reversals such that a magnetic stripe reader can read the flux-reversals from the static magnetic track. Persons skilled in the art will also appreciate that a magnetic emulator may communicate information that remains the same from payment card transaction to payment card transaction (e.g., static information) as well as information that changes between transactions (e.g., dynamic information).

A card may include magnetic emulators without, for example, including a static magnetic track. Read-head detectors may also be provided. Persons skilled in the art will appreciate that a magnetic reader may include the ability to read two tracks of information (e.g., may include at least two read-heads). All of the information needed to perform a financial transaction (e.g., a credit/debit card transaction) may be included on two magnetic tracks. Alternatively, all of the information needed to perform a financial transaction (e.g., a gift card transaction) may be included on one magnetic track. Accordingly, particular cards, or other devices, may include the ability, for example, to only transmit data associated with the tracks that are needed to complete a particular financial transaction. Persons skilled in the art will appreciate that for systems with three tracks of information, the bottom two tracks may be utilized for credit card information. Persons skilled in the art will also appreciate that a secure credit card transaction may be provided by only changing, for example, one of two magnetic tracks utilized in a credit card transaction (for those transactions that utilize two tracks). Accordingly, one track may be a static magnetic track constructed from a magnetic material and the other track may be provided as a magnetic emulator. Persons skilled in the art will also appreciate that numerous additional fields of data may be provided on a magnetic track in addition to a credit card number (or a security code). Dynamic information may be provided in such additional fields in order to complete a particular financial transaction. For example, such additional dynamic information may be numbers (or characters), encrypted with time and synced to software, at a validating server, operable to validate the encrypted number for a particular period of time.

Card 250 includes emulator 251 that includes a coil operable to communicate data serially to a magnetic stripe reader. Similarly, for example, emulator 251 may receive information for a magnetic stripe encoder. Persons skilled in the art will appreciate that a coil may run across the length of a card such that a read-head moves along the length of the coil and can receive information transmitted serially from the coil. The coil may extend into multiple tracks such that multiple read-heads receive information from the coil. Track information can be sent serially (e.g., track 1 information followed by track 2 information). Multiple coils may be driven separately and placed in different zones such that a single read-head moves from coil-to-coil (e.g., zone-to-zone) and power is conserves as only coils in a particular zone (or zones) may be utilized to communicate information any particular time. Separate coils may be utilized for separate tracks. Materials may be placed in the interior of each coil to assist with manipulating the electromagnetic field produced by the coils. Material may be placed above or below a coil to further manipulate the electromagnetic field produced by the coil. Switching circuitry 252 may include, for example, one or more transistors that may be utilized to control the direction of current via emulator 251 (e.g., the polarity of voltage(s)) across a drive resistor). For example, a coil may be utilized to transmit a string of information to a particular read-head. Different coils may transmit information at different speeds (or at the same speed). Different coils may transmit different amounts of information. For example, three coils may be provided. The coil closest to the bottom of the long-end of a card may transmit at least 79 characters. The coil next closest to the bottom of the long-end of a card may transmit at least 40 characters of information. The coil next closest to the bottom of the long-end of the card may transmit at least 107 characters. One or more coils may have different character sets (e.g., a 6-bit character set or a 7-bit character set). The last bit in a character may include, for example, a parity bit. Additional synching information may be transmitted before and after the data information to assist with synching a magnetic stripe reader. For example, a string of zeros may be communicated before and after communicating primary data. Characters may be included in the data information for other purposes such as an LRC character.

FIG. 3 shows card 300 that may include a number of components. Card 300 may include one or more processors 320. A processor may include, for example, cache memory, RAM, and/or ROM. Additional memory may be provided on card 300. For example, additional non-volatile, volatile, cache memory, RAM, and/or ROM may be provided on card 300. Battery 325 may be provided on card 300. Battery 325 may be, for example, a lithium polymer battery and may have a thickness less than a millimeter (e.g., approximately 0.5 mm). RFID antenna 315 may be provided on card 300 and may communicate data to an RFID reader. Persons skilled in the art will appreciate that an RFID may be included that is a passive or active RFID. IC chip 310 may be included on card 300 and may communicate data to an IC chip reader. Device 301 may be included to communication information to a magnetic stripe reader. Device 301 may include any number of magnetic emulators, magnetic encoders that encode magnetic stripes, and/or magnetic stripes. For example, device 301 may include a magnetic emulator for one track of magnetic data and a magnetic stripe for a second track of data. Alternatively, for example, device 301 may include two emulators for separate tracks of data. An emulator may, for example, communicate information to a read-head of a magnetic stripe reader serially. One or more read-head detectors 302 may be provided to detect a read-head (or other attribute)

of a magnetic stripe reader. Additional detectors may be included to detect, for example, when a card is provided into an IC chip reader and/or an electromagnetic field from an RFID reader. Button array 330 may be provided, for example, to receive input from a user. Button array 330 may include any number of buttons (e.g., 4, 5, 10, or more than 10). Button array 330 may include, for example, mechanical buttons, capacitive buttons, or any type of user interface. One or more displays 340 may also be included. A display may be, for example, an electronic ink display (e.g., electrochromic display), LCD display, or any other type of display. Display 340 may be flexible.

Display 340 may be printed onto a layer during a printed fabrication process (e.g., PCB). Additionally, for example, battery 325 may be printed onto a layer during a printed fabrication process (e.g., PCB). Similarly, a magnetic emulator may be printed onto a layer during a printed fabrication process (e.g., PCB). Other components may be printed onto a layer during a printed fabrication process (e.g., PCB) such as capacitive read-head detectors, and capacitive touch sensors. Accordingly, a display, battery, read-head detector, and button array may be printed on one or more layers that are bonded together and laminated.

FIG. 3 shows card 350 that may include, for example, processor 353, switching circuitry 352, and emulator 351 having active region 354. Switching circuitry 352 may, for example, control the direction of current through emulator 351 in order to change the direction of electromagnetic fields generated by emulator 351 such that data may be communicated serially to a magnetic stripe read-head. Persons skilled in the art will appreciate that emulator 351 may be fabricated on a single layer and that region 354 may include coil segments dense enough to generate an electromagnetic field that can be recognized by a read-head of a magnetic stripe reader.

Figure 4:
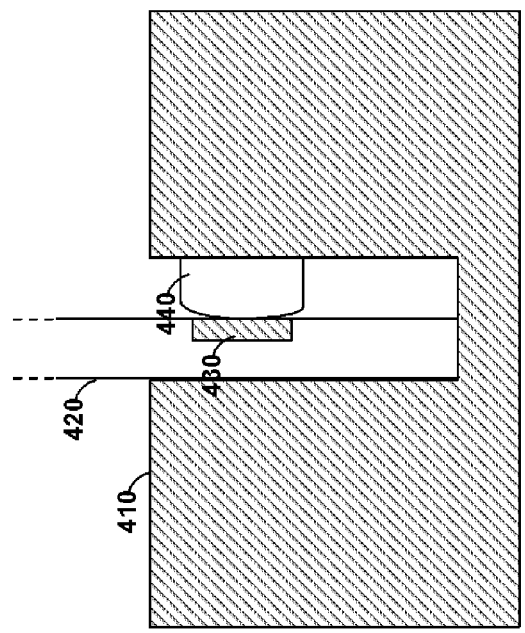
FIG. 4 is an illustration of a card and a reader constructed in accordance with the principles of the present invention.

FIG. 4 shows environment 400 that may include magnetic stripe reader 410, read-head housing 440, card 420, and magnetic emulator 430. Read-head housing 440 may include any number of read-head's such as, for example, one, two, or three read-heads. Each read-head may independently receive magnetic fields from magnetic emulator 430 (or a magnetic stripe, such as a magnetic stripe encoded on-card by card 420). Emulator 430 may be positioned to be adjacent to any one or more read-heads of read-head housing 440 or may be positioned to communicate information to any one or more read-heads of read-head housing 440. Persons skilled in the art will appreciate that emulators with longer lengths may be located within the proximity of one or more read-heads for a longer duration of time when a card is swiped. In doing so, for example, more information may be transmitted from an emulator to a read-head when a card is being swiped.

Figure 5:
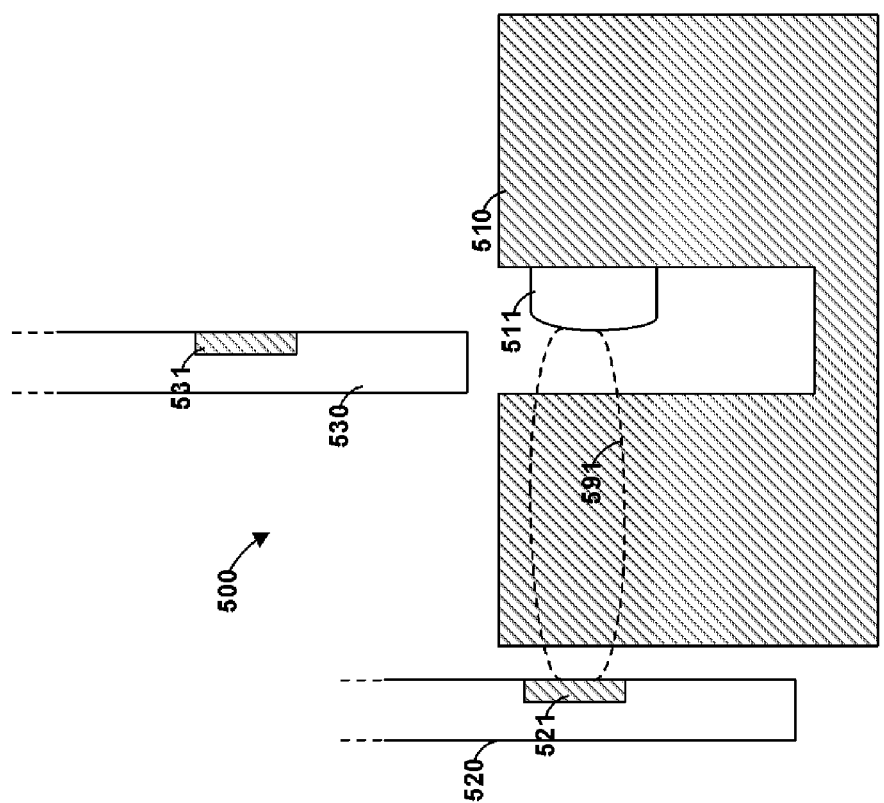
FIG. 5 is an illustration of a card and a reader constructed in accordance with the principles of the present invention.

FIG. 5 includes environment 500 that may include cards 520 and 530 as well as magnetic stripe reader 510. Read-head housing 511 may be included on a wall of a trough of magnetic stripe reader 510. The trough may be sized to accept cards (e.g., credit cards).

Card 520 may include emulator 521. Emulator 521 may provide electromagnetic field 591 that may transmit through a portion of the housing of magnetic stripe reader 510 (e.g., through a wall of a trough to get to read-head housing 511). Accordingly, card 520 may be located outside of a reader—yet still be operable to communicate information to a magnetic stripe reader. A reader may be provided with an outer wall, for example, with a thickness of a quarter of an inch or more. Emulator 521 can provide electromagnetic field 591 over a distance of, for example, a quarter of an inch or more.

Persons skilled in the art will appreciate that card 520 may be coupled to a device via a permanent or removable cable. Such a device may provide power to card 520 as well as control information—such as control information for emulator 530. An external source of power may be utilized, for example, to provide a larger amount of electrical energy to emulator 521 than from a source of power located within card 520. Persons skilled in the art will appreciate that a car having an internal battery may still be able to receive a cable from a device having its own source of electrical energy.

Card 530 may be provided with emulator 531 and may electrically couple with a read-head of magnetic stripe reader 510. Any number of emulators may be provided in card 530 in any number of orientations such that the appropriate electromagnetic field may couple with a read head of read-head housing 511 regardless of the orientation of card 720 with respect to read-head 511. More particularly, for example, additional read-head housings may be provided in magnetic stripe reader 510 at different locations about the reader to electrically couple with a emulators in a number of different configurations. A sticker and/or guide-structures may be provided on a magnetic stripe reader to, for example, direct a user on how to position his/her card (or other device) for contact-less transmission of data (e.g., credit card data) to a read-head housing without using the trough that includes that read-head housing.

Persons skilled in the art will appreciate that a magnetic stripe reader may include a trough that includes two (or more) read-head housings 511 located in approximately the same vertical position on a card-swiping trough, but at different horizontal locations on opposite walls of the trough. In doing so, for example, a magnetic stripe may be read regardless of the direction that a card having the magnetic stripe is facing when the card is swiped. Magnetic emulator 521 may, for example, communicate magnetic fields outside both the front and read surfaces of a card. Accordingly, a single emulator 521 may, for example, couple with a single read-head regardless of the direction the card was facing when swiped. In doing so, for example, the costs of readers may be reduced as only a single read-head may be need to receive information regardless of the direction a card is facing when swiped. Accordingly, magnetic readers do not need stickers and/or indicia to show a user the correct orientation to swipe a card through a magnetic stripe reader. An adapter may be provided that coupled directly to a read-head that allows a device not operable to fit in a trough to electrically couple with a read-head.

An emulator may be positioned about a surface of a card (or other device), beneath a surface of a device, or centered within a card. The orientation of a magnetic emulator in a card may provide different magnetic fields (e.g., different strength's of magnetic fields) outside different surfaces of a card. Persons skilled in the art will appreciate that a magnetic emulator may be printed via PCB printing. A card may include multiple flexible PCB layers and may be laminated to form a card using, for example, a hot and/or cold lamination. Portions of an electronic ink display may also be fabricated on a layer during a PCB printing process.

Persons skilled in the art will appreciate that a number does not need to, for example, change with time. Information can change, for example, based on manual input (e.g., a button press or combination of button presses). Additionally, a credit card number may be a static display number and may be wholly or partially displayed by a display. Such a static credit card number may result in the reduction of fraud if, for example, a personal identification code is required to be entered on a manual input entry system to activate the display.

Additionally, fraud associated with card cloning may be minimized with the use of a magnetic emulator activated by the correct entry on a manual input entry system.

Person skilled in the art will also appreciate that a card may be cloned by a thief, for example, when the thief puts a illegitimate credit card reader before a legitimate credit card reader and disguising the illegitimate credit card reader. Thus, a read-head detector may detect a read-head housing and then, if a second read-head housing is detected on the same side of the credit card, the reader may transmit information to the second read-head that signifies that two read-head housings were detected. In doing so, for example, a bank, or the police, may be notified of the possibility of the presence of a disguised cloning device. The information representative of multiple read-heads may be included with information that would allow a credit card number to be validated. As such, a server may keep track of the number of read-head housings at each reader and, if more read-head housings are detected than expected, the server may contact an administrator (or the police). The server may also cause the credit card transaction to process or may reject the credit card transaction. If the number of read-head housings (or read-heads) is the number expected by the server, the server can validate the payment transaction.

A payment system using dynamic numbers may, for example, be operable with numbers that are stored outside of the period in which those numbers would otherwise be valid. A server may be included, for example, that accepts a dynamic credit card number, information representative of a past credit card number, and the merchant that is requesting payment. The server may register that merchant for that saved number. The number may be decrypted (or otherwise validated) for that past period of time. Accordingly, the credit card transaction may be validated. Additionally, the merchant identification information may be linked to the stored dynamic credit card number for that past period of time. If the server receives a transaction from a different merchant with that same dynamic credit card number for that same period of time, the server may reject the transaction. In doing so, a merchant may be protected from having credit card numbers stolen from its various storage devices. If a thief steals a number from a merchant's server that is associated with a past period of time, that number cannot be used, for example, anywhere else. Furthermore, such a topology may, for example, allow merchants to provide a one-click shopping, periodic billing, or any other type of feature that may utilize dynamic numbers that are stored and used outside of the period in which the dynamic numbers were generated.

Persons skilled in the art will appreciate that different emulators may be controlled by different switching circuitry (e.g., different transistors).

Persons skilled in the art will appreciate that multiple buttons may be coupled together to form a single-bit bus. If any button is pressed, the bus may change states and signal to the processor to utilize different ports to determine what button was pressed. In this manner, buttons may be coupled to non-triggerable ports of a processor. Each button (or a subset of buttons) may be coupled to one or more triggerable ports of a processor. A port on a microprocessor may be utilized to drive an emulator in addition to, for example, receiving information from a button. For example, once an appropriate personal identification code is received by a processor, the processor may utilize one or more ports that receive information from one or more buttons to drive an emulator (e.g., for a period of time). Alternatively, for example, a magnetic emulator may be coupled to its own triggerable or non-triggerable processor port. A card may also include a voltage regulator to, for example, regulate power received from an internal or external source of power.

Persons skilled in the art will appreciate that any type of device may be utilized to provide dynamic magnetic information on a card to a magnetic stripe reader. As discussed above, a magnetic encoder may be provided that can change information on a magnetic medium where the changed information can be detected by a magnetic stripe reader.

Persons skilled in the art will appreciate that the direction of current through magnetic circuit 650 may be changed and controlled in a pattern that is representative of magnetic stripe data. Particularly, a processor may, for example, transmit information through a coil by changing the direction of the electromagnetic field generated from emulator circuit at particular times. A change in the frequency of field reversals may be representative of, for example, a particular bit of information (e.g., "1" or "0").

Figure 6:
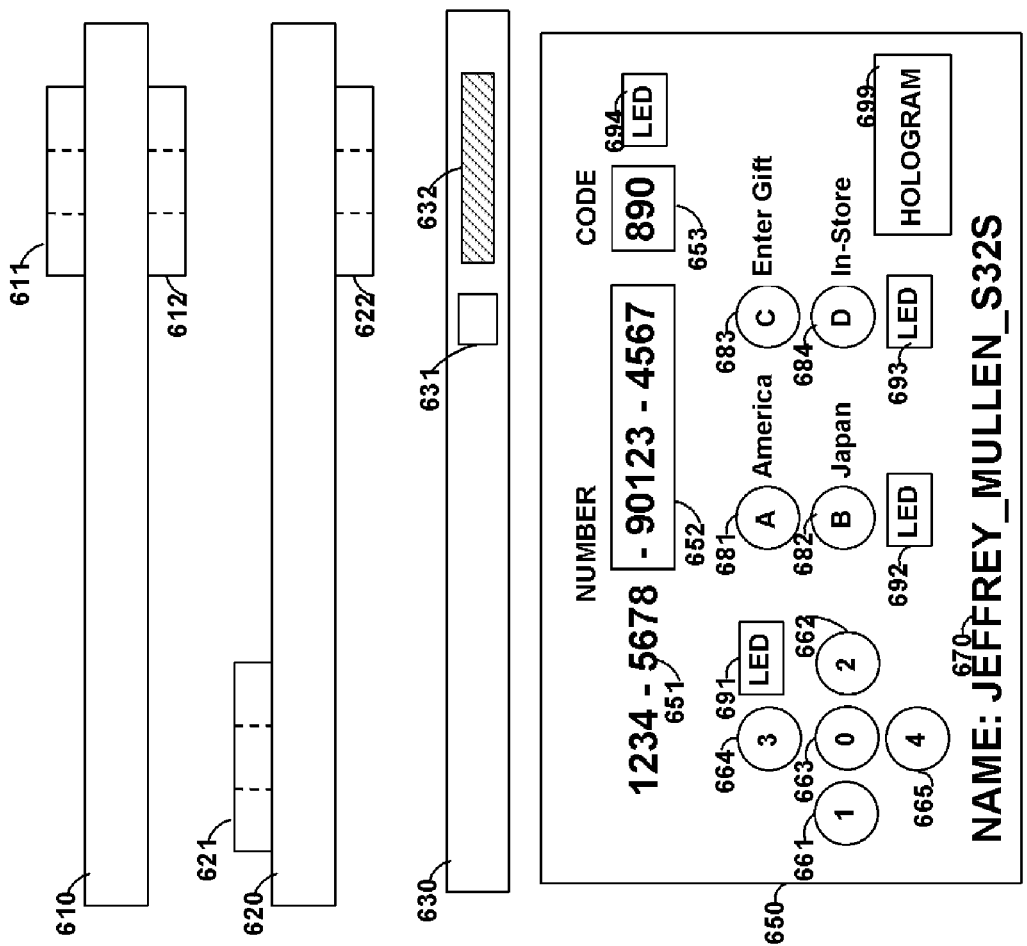
FIG. 6 is an illustration of a cards constructed in accordance with the principles of the present invention.

FIG. 6 shows card 610, which may include magnetic stripe 611 and magnetic stripe 613. A magnetic stripe may, for example, have multiple tracks. Each track may be fabricated from, for example, a different magnetic stripe material. Magnetic stripe 611 may include data structured to be received by the infrastructure for one country. Magnetic stripe 612 may include data structured to be received by the infrastructure for another company. Magnetic Stripe 612 and 611 may be aligned vertically. Accordingly, a user may place card 300 into a reader from one country in one direction and the user may place card 300 into a different reader from a different country in a different direction. The information included on magnetic stripe 611 and 612 may be associated with a user's payment card account such that purchase to both territories posts to the same account. Card 620 may include, for example, magnetic stripe 621 and 623 that includes payment card data operable for use in different territories. Magnetic stripe 621 and 623 may be provided such that magnetic stripe 621 and 623 are not vertically aligned with one another. Card 630 may be included that may include direction detector 631. A card may determine the direction the card is facing via direction detector 631. Accordingly, the card may determine which territory the user of the card believes he/she is located in. Accordingly, magnetic emulator 632 (or a magnetic encoder) may be utilized to communicate the appropriate territory-based payment information through magnetic emulator 632. Persons skilled in the art will appreciate that direction detector 631 may be, for example, a read-head detector. Accordingly, read-head detector 631 may be utilized to determine the side facing a read-head detector such that the payment information associated with that side's territory is communicated. An RFID antenna and/or smart-chip may be provided with information in a similar manner by detecting the orientation of a card with respect to a reader. Persons skilled in the art will appreciate that multiple emulators (or encoders) may be utilized instead (e.g., one for each track). Similarly, for example, two arrays of magnetic emulators may be utilized instead of the two magnetic stripes—each array located on a different end of a card (e.g., at the ends where magnetic stripe 621 and 622 of card 620 are located).

Card 650 includes buttons 651-664, light sources 691-694, displays 852-853, permanent information 651 and 670, buttons 681-684, and hologram 699. A user may be provided with a payment number. Such a payment number may be comprised of permanent data, dynamic data, or a combination of permanent and dynamic data. Dynamic data may be provided, for example, on display 652. Display 653 may be utilized to provide a code, which may be dynamic. Such a code may be utilized in authorize a transaction. Persons skilled in the art will appreciate that displays may display a code, payment number, or any type of data that changes based on time or based on use (e.g., utilizes one-time use data). Similarly, data may be static and may not change. Accordingly, for example, a display may be utilized to display the same data when desired such that the data may be hidden when the data is not desired to be displayed. Buttons 651-664, 681-682, and/or 683-684 may be utilized to signal a processor to display information on display 652, display 643, or display 652 and display 653.

A Personal Identification Code (PAC) may be entered to utilize to display data, as well as instruct a processor to provide particular data. For example, a particular PAC may provide one payment number (e.g., a credit card number) while a different PAC may provide a different payment number (e.g., a debit card number). A PAC may include a sequence of button presses (e.g., 5 particular button presses). Furthermore, a PAC may be utilized to unlock a card so that the card may be utilized. For example, buttons 681, 682, 683, and 684 may not be utilized by a user until an appropriate PAC has been entered via buttons 651-665. A number may be changed based on time (e.g., via display 652, display 653, or display 652 and display 653). Accordingly, a PAC may be entered such that the particular number associated with a particular button (e.g., a number associated with button 651) for a particular time period (e.g., a particular day) may be displayed. One PAC may activate display 652 while another PAC may activate display 653.

Light source 691 may be an LED or other source of light. Light source 691 may display light each time a button associated to light source 691 is pressed (e.g., buttons 661-662). Similarly, light source 692 may display light each time a button associated with light source 692 is pressed (e.g., button 681 or 682). Light source 693 may display light each time a button associated with light source 693 is pressed (e.g., light source 683 or 684). Light source 694 may be associated to a component and may display light each time that component is activated (e.g., display 653 or 652 is activated). Light sources may emit light having different colors. For example, a processor may determine that a PAC provided to the processor via buttons 661-665 matches a valid PAC for performing an operation. Each button press may cause light source 691 to emit light of a first color (e.g., YELLOW). The last button press to complete the PAC, however, may cause light source 691 to emit a different color if the PAC is VALID (e.g., emit GREEN) yet emit another color if the PAC is INVALID (e.g., emit RED). Particular areas of a laminated card may be transparent such that light from a light-source illuminates the transparent area.

Button 681 may be associated with a card of a particular country. Persons skilled in the art will appreciate that a card may be provided with a default number. Such a default number may include, for example, permanent data 651 and data displayed on display 652. Accordingly, a particular PAC may display the default data on display 652.

Persons skilled in the art will appreciate that other default data may be provided to other components of a card upon entry of a PAC. For example, particular default data (e.g., payment card number and discretionary data) may be communicated to a magnetic emulator (or magnetic encoder) such that the information may be communicated to a magnetic stripe read-head. Similarly, default data (e.g., payment card number and discretionary data) may be communicated to an RFID antenna, an IC chip, or an RFID antenna and an IC chip. Such default data may be different for each component (e.g., magnetic encoder/emulator, RFID antenna, IC Chip) and may be in different formats (e.g., one track of payment data for one magnetic emulator and another track of payment data for another magnetic emulator).

Button 681 may cause, for example, display 652, display 653, or display 652 and 653 to display data associated to button 681. Similarly, data associated to button 681 for other components of card 650 (e.g., a magnetic emulator, magnetic encoder, RFID antenna, and IC chip) may be communicated through those components. Button 681 may be associated with, for example a particular territory (e.g., America). Accordingly, for example, information communicated via card 650 may be associated with a default country upon entry of a particular PAC until, for example, a button is pressed associated with a different country. At this time, for example, the information communicated by card 650 may change to the information associated with the particular button pressed. Button 692 may be provided for a country different than, for example, a default country and a country associated with another button (e.g., button 681). A card may not be associated with a default country such that, for example, a button is pressed to determine the type of information communicated by a card.

A card, or other device, may autonomously determine, for example, the location of the card such that the appropriate information is communicated. For example, a GPS receiver (or another type of antenna) may be utilized to determine the location of the card, or other device (e.g., mobile telephone), such that the appropriate information is transmitted. Accordingly, a card, or other device, may send American payment data when the card, or other device, is located in America. However, the card may send Japanese payment data, or other data, when the card is located in Japan. Display 652 and/or display 653 may display different amounts of information based on the country scheme utilized. Similarly, other components such as magnetic emulators, magnetic encoders, RFID antennas, and IC chips may utilize different amounts of information based on the type of country utilized.

Button 683 may be utilized to provide instructions to a processor that a gift card is desired to be utilized via card 650. A gift code may be entered (e.g., via buttons 661-665) after button 683 is pressed such that a user may, for example, associate a gift card to card 650. Accordingly, card 650 may be utilized to make a gift purchase such that the original gift card may be thrown out (or left at home). The code entered into card 350 may be utilized, for example, to provide a processor with a number to transmit via the card (e.g., next time button 683 is utilized). Such a number (as well as associated data such as associated discretionary data) may be communicated by card 650 via one or more displays, magnetic emulators, magnetic encoders, RFID antennas, and IC chips. A code may alternatively, for example, transmit a flag (e.g., discretionary data) that a gift card is being utilized (e.g., upon another use of button 683) such that a server may look at a seller ID number and check if there are any gift cards associated to a particular payment card number for that seller ID number. Accordingly, for example, a user may obtain a gift card (e.g., Target gift card) and may link that gift card to his/her payment card account (e.g., credit card account) and may utilize a button (e.g., 683) to send a flag that a gift card is desired to be utilized. A code may be entered to provide a particular flag (e.g., a flag associated with a particular seller). Alternatively, no code may be entered and button 683 may just be utilized to generate a generic flag (e.g., causing a server to check if there are any linked gift cards for the account associated with the seller associated with the utilized point-of-sale reader). A user may be provided with a particular code to be entered when utilize the gift card at an online store (e.g., Target's online store). The online store may, for example, allow a user to enter his/her payment information (e.g., credit card number, expiration date, name on card, zip code associated with card) and allow the user to select whether a gift card should be utilized associated with that card (e.g., via a radio button or other webpage input structure).

Button 684 may be provided. Button 684 may be utilized, for example, to make an in-store purchase. Button 684 may activate, for example, display 652 but not display 653. Code 653 may be utilized, for example, to at least complete a particular online transaction. In not activating display 653, for example, a user that is provided with a card during an in-store purchase may not gain access to information displayed on display 653. Persons skilled in the art will appreciate, for example, that the information on display 653 may be transmitted via a component (e.g., emulator) even though the information is not displayed. Moreover, for example, display 652 and 653 may be the same display but that a particular interface (e.g., button) may display information on different portions of the display.

Figure 7:
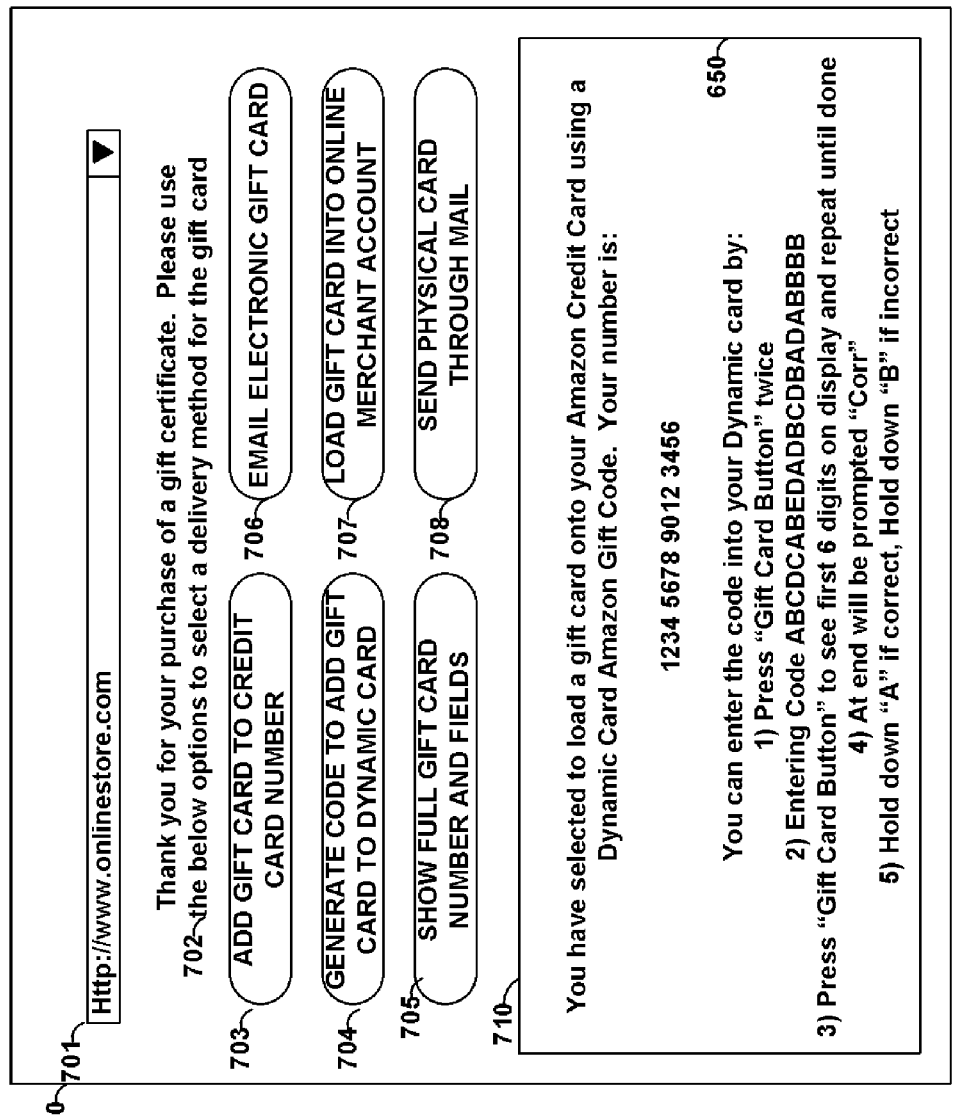
FIG. 7 is an illustration of a webpage constructed in accordance with the principles of the present invention.

FIG. 7 includes webpage 700 that may include, for example, navigational tool 701 that may be utilize to navigate through different pages of a website or different websites of an intranet or internet. Information 702 may be displayed, for example, when a user purchases a gift certificate online or purchases a gift certificate in a store and attaches that gift certificate to the users account online. Interface 703 may be utilized by a user, for example, to add the particular gift card to their payment account. Such a payment account may be a credit account, debit account, check account, or any other type of payment account. A gift card may be linked to such an account such that a user does not have to, for example, carry around multiple cards. The user may, for example, carry around a single card, but a server may recognize whether a user has a gift card associated with a particular seller (e.g., based on a seller ID communicated from the point-of-sale device or other server). A user may add, modify, delete, or transfer gift cards associated to a payment account. Thus, for example, a user may receive a gift card for Christmas, may link the gift card to his/her payment account (e.g., credit card account), and may utilize the gift card by utilizing his/her card associated with his/her payment account. Interface 706 may be utilized, for example, to email an electronic gift card to a user. Interface 708 may be utilized to send a physical card through the mail to a user such as the user that purchased the gift card or a friend of the user that purchased the gift card. Interface 707 may be utilized to load the gift card onto a merchant account. For example, a gift card that is purchased in a store (e.g., Walmart) may be entered into a website associated with that user's payment card (e.g., Bank of America) and then transferred to a merchant's website (e.g., Walmart). Persons skilled in the art will appreciate, for example, that a gift card may not be active until purchased. Activation may occur in a variety of ways. For example, a card may be activated by a cashier that completes a purchase of a gift card—thus communicating data to a server that activates that gift card. Similarly, a gift card number generated online may be activated upon generation. Persons skilled in the art will appreciate that pre-paid payment cards such as pre-paid debit cards may be utilized as gift cards are utilized.

Interface 704 may be utilized, for example, to generate a code that may be utilized to add a gift card to a dynamic card. Interface 705 may be utilized to show a full string of data that a credit card may utilize to communicate to an input device. For example, the full string of data may be the data that may be displayed and entered into a website to use the gift card. Alternatively, the data may be one or more tracks of magnetic stripe data (e.g., card number, name, and discretionary data). Alternatively still, for example, the data may be RFID antenna data or IC Chip data.

Persons skilled in the art will appreciate that a payment card may be associated with a company. For example, TJX may issue a TJX credit card. Such a card may offer incentives if the card is utilized within the company (e.g., within a TJX store). The gift cards of such a store may have data that is the same from gift card to gift card (e.g., the first digit or digits of a gift card number may be the same as they may be utilized to route data to a particular network). Accordingly, such a payment card may include a gift card functionality that accepts TJX gift cards. A user may be able to, for example, load in the control portions of the data such that the user does not have to enter in data that may be the same for all TJX cards. In doing so, for example, the amount of time utilized to enter information may be minimized.

Persons skilled in the art will appreciate that data may be transferred, such as gift card and/or pre-paid card data, to a card in a variety of ways. For example, a card may be swiped a second time through a magnetic stripe reader that includes a magnetic stripe encoder. A coil on the card may be utilized to receive the information and provide the received information to a processor. In doing so, information may be loaded into the card. Similarly, an IC chip may be utilized to receive data as well as a passive or active RFID. Additionally, one or more microphones may be included to receive audio information that may be representative of data. Accordingly, for example, a user may hold his/her card, or other device, next to a device that is operable to transmit audio via a speaker (e.g., laptop, stationary computer, or mobile telephonic device). The audio information may be discerned by the card and utilized to load information into the card (e.g., a gift card or pre-paid card. An application may also be loaded that enhances the functionality of the card. Such an application may include, for example, a user's medical information such that medical information can be displayed via the card (or other device) during a medical emergency. Accordingly, applications and/or payment cards may be purchased online and a speaker may communicate information to a card. Similarly, the card may include a speaker for transmitting information such that bi-directional communications are established. A light detector may be provided on a card that may receive light pulses indicative of data. Accordingly, for example, a user may hold a card up to a display—such as the screen of a laptop, stationary computer, or mobile phone—and information may be communicated from the display to the card via the light detector. Similarly, a light source may be utilized to communicate information from one device to another. For example, a light source (e.g., LED) may be utilized to communicate information from one card to another. Similarly, a magnetic stripe reader may include a light source. A card may be positioned over the light source such that a light detector of the card is aligned with the light source to receive light. Accordingly, the light of a magnetic stripe reader (or other type of reader) may be utilized to communicate information back to a card. A user may utilize interfaces on the card (e.g., buttons) to initiate a transfer of data from one card to another card or from a device to a card. A variety of types of data may be communicated. For example, money may be communicated from one debit card to another debit card such that payments may occur between the cards. Accordingly, for example, the next time a card is utilized via a reader (e.g., a magnetic stripe reader) information of the transfer may be communicated to a server for processing. Light may be utilized to transfer data from a card to a computer using, for example, a camera (e.g., webcam) on the computer. Sound may be utilized to transfer data from a card to a computer using, for example, a microphone on the computer.

A interface (e.g., a button) may be activated (e.g., pressed) for a period of time and different actions may be associated with different durations of activation. Different combinations of interfaces (e.g., different buttons) may be held together at the same time to perform a variety of functions. For example, a master unlocking code may be provided in case a card becomes locked (e.g., too many incorrect PACs were entered in a row). To enter a master unlocking code, a particular set of buttons may first need to be pressed in combination.

Information 710 may be displayed on webpage 700. Information 710 may, for example, describe that a selection occurred as a result of user input that was indicative of requesting that a gift card be loaded onto a credit card using a code. The information may include instructions for loading the code. For example, a button may be requested to be pressed once. Then, a code may be requested to be entered into the card. Next, a button may be requested to be pressed to display a particular portion of the code to confirm that the particular portion was correctly entered. This process may repeat until the entire code is confirmed as having been correctly entered. The information may include how a card may respond (e.g., via displaying information, providing light in a particular manner, vibrating in a particular manner, or providing sound in a particular manner). To confirm an entry is correct, the user may be requested to perform a particular action such as, for example, holding down a particular button if the entry was correct.

A display may also be utilized as an interface. For example, a display may include a contact and an electronic ink. The electronic ink may change colors in response to, for example, a particular electrical signal being supplied to the contact. A capacitive sensor may be coupled to such a contact, however, such that a user interaction with the contact may be sensed by the capacitive sensor. Accordingly, a card may include a display that can also receive user input. Persons skilled in the art will appreciate that a display may include multiple contacts. For example, a display may include multiple 7-segment (e.g., to display digits) or 11-segment, 14-segment, or 16-segment (e.g., to display alphanumerics) regions where each segment may be coupled to a capacitive sensor.

A biometric sensor may be placed on a card or other device. Such a biometric sensor may be, for example, a fingerprint reader. Accordingly, one or more fingerprints may be stored in the memory of a card and compared to scanned fingerprints. Different fingerprints may activate the card differently (e.g., utilize a different user's payment card info).

Figure 8:
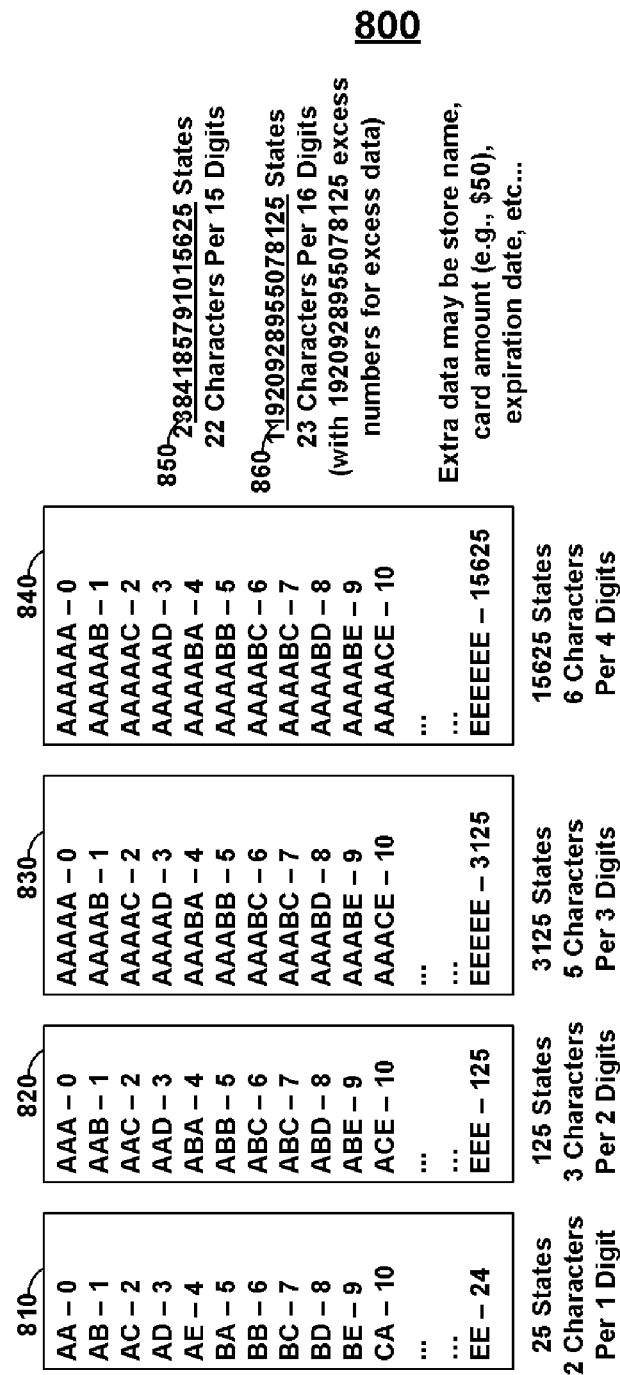
FIG. 8 is an illustration of a language scheme constructed in accordance with the principles of the present invention.

FIG. 8 shows mapping scheme 800. Mapping scheme 810 may be utilized. Any number of interfaces (e.g., buttons) may be placed on a card. For example, four or five buttons may be placed on a card. A button may be associated with, for example, a color, number, letter, or symbol. Payment card numbers, however, may have a digit base. Accordingly, mapping may be utilized such that different combinations of colors, numbers, or symbols may be associated with a digit. For example, suppose five buttons are provided and each button is associated with a letter between A and E. Mapping scheme 810 may be utilized to allow a user to input digits. Accordingly, for example, a processor may include such a table such that the processor may be able to translate incoming information from a user such that digits may be communicated (e.g., via a display, encoder, emulator, RFID, and IC chip). Two characters from a five-button combination may, for example, provide for 25 different states. Scheme 820 may be provided in which 3 character sets (where each character has 5 possibilities) provides 125 states. Accordingly, a 3 character set may provide 2 digits of information. Scheme 830 may be utilized, for example, to provide 3 digits of information with a 5 character set. Scheme 840 may be utilized, for example, to provide 4 digits of information with a 6 character set. Scheme 850 may be utilized to provide 15 digits of information with a 22 character set. Scheme 860 may be utilized to provide, for example, 16 digits of information with a 23 character set (where each character has one of five possibilities).

Persons skilled in the art will appreciate that numerous numbers may not be utilized by a company. For example TJX may only be provided with 15,000 pre-paid debit card numbers. Such numbers may be, for example, 19 digits in length. Suppose, for example, that TJX issued a payment card that allowed for TJX pre-paid debit cards to be entered into a the TJX payment card. Accordingly, albeit a number is 19 digits, a mapping may allow a user to enter a card number with only 6 characters. Accordingly, for example, a 19 digit number may be entered into a card using less than 19 button activations. Numbers may be encrypted based on time to increase security as these numbers are communicated from a card (e.g., via an emulator, encoder, display, RFID, and IC chip).

Persons skilled in the art will also appreciate that additional information may be communicated with a code. For example, the type of gift card (e.g., a TJX gift card) may be communicated with the code. Additionally, the amount of the gift card, the balance of the gift card upon code generation, the expiration date of a gift card, as well as a message provided by the purchaser of the gift card may be communicated via a code.

Persons skilled in the art will appreciate that a user's payment card number (e.g., credit card or debit card number) does not have to change. A display may hide this payment card number until an appropriate unlocking code is entered into buttons of the card. Similarly, a magnetic emulator may not be provided current until the proper unlocking code is entered—thus keeping magnetic information private and not allowing undesirable readers to read a card. A security code may be displayed on the same or a different display. A button may be provided representative of an online purchase (or a user may utilize buttons to instruct the processor that an online purchase is desirable). For such an online purchase, the credit card number and the security code may be displayed—but the magnetic emulator may not be activated. In doing so, the level of security of the card is increased. Furthermore, for example, a button may be provided representative of in-store purchases (or a user may utilize buttons to instruct the processor that an in-store purchase is desirable). Accordingly, a processor may be signaled that an in-store purchase is desired. A different operation may be associated with different types of purchases (e.g., online or in-store). Accordingly, for example, magnetic emulators may be activated for an in-store environment—but not the displays. Accordingly, for example, a restaurant cashier may not be able to read the credit card number from the card, but may still be able to swipe the card. If a reader is down or a cashier requires reading particular information (e.g., a security code or credit card number information) then controls may be utilized to communicate this information. A record of the types of transactions may be stored and may be communicated in discretionary fields of data within a transmitted data track. Such record information may be utilized, for example, to further increase security and/or introduce a variety of additional functionality.

Different types of cards may be provided on a card. For example, a security ID number and a credit card number may both be provided on the same card. A button may be utilized to allow a user to provide instruction to a processor such that the processor can display (e.g., visually and/or magnetically) the desired information. For example, a user may determine to use one of a variety of payment accounts (e.g., credit and/or debit) for a purchase. An entire payment number (e.g., credit or debit) may be changed and/or hidden visually and/or magnetically. A portion of a payment card number (e.g., credit or debit) may be changed and/or hidden visually and/or magnetically.

Persons skilled in the art will appreciate that a display on the card may display a credit card number that does not change with time (or transaction or button press). Additionally, for example, a magnetic emulator (or multiple magnetic emulators) may magnetically communicate financial data that does not change with time. Such a card may reduce, for example, the effects of physical card theft and card cloning.

Persons skilled in the art will appreciate that any numbers of a credit card number may remain static and/or change either with time or based off a transaction (e.g., by sensing a read-head "swipe"). Additionally, any static and/or dynamic numbers may be displayed via a display or printed on a card. For example, a middle 6 digits of a credit/debit card number may be static and may be displayed on a display. Such a middle 6 digits may be displayed, for example, upon the entry of a correct PIC. Similarly, a magnetic emulator may not communicate information until a correct PIC has been entered by a user. Doing so may, for example, reduce fraud associated with card cloning. Additionally, a receipt may be provided that includes masked credit card numbers except for the last few digits of credit card numbers. Accordingly, displaying a static middle 6 digits of credit card numbers may allow for such a receipt to be provided while still reducing credit card fraud from hiding numbers that are not displayed on such a receipt. Any amount of numbers and/or characters may be displayed through a display. For example, nineteen digits may be displayed as part of a credit/debit numbers and these numbers may also be communicated through one or more magnetic emulation circuits. The entry of particular PICS may provide different results. For example, a first PIC may only display a string of alphanumeric characters. A second PIC may only activate a magnetic emulation circuit to transmit information including that string of alphanumeric characters (or a different string). A third PIC may activate a magnetic emulation circuit and a display. A display and/or magnetic emulation circuit may be turned OFF, for example, upon entry of an incorrect PIC and/or after a period of time has passed since the entry of the PIC and/or after the detection of a particular number of swipes by a read-head detector (e.g., one or two).

Persons skilled in the art will appreciate that a credit/debit card number (or any other information) may remain static until an event occurs and then may become dynamic (e.g., change based on swipes and/or time). For example, a particular PIC may change from a static to a dynamic topology and/or a topology may be changed from static to dynamic after a pre-determined period of time. Additionally a card and/or device may include a wireless receiver and a topology may be changed from a static to a dynamic topology upon, for example, receiving an appropriate signal from the wireless receiver. Accordingly, a validation process may change at a validation server depending upon whether a card is utilizing a static and/or dynamic topology at any given time. Additionally, a static credit/debit card number may be printed on the face of a card and information (e.g., a security code) may be displayed via a display and remain static over time (or with use) or be provided dynamically.

A card or other device (e.g., a mobile telephone) may accept a pre-determined number of consecutive incorrect PICS before locking the card for a period of time or until an appropriate secondary PIC is entered. Accordingly, a user may enter in an incorrect PIC a number of times and then, after a card becomes locked, call a support center for a secondary one-time use PIC. A card may cycle through unlocking PICS based, for example, on time or the number of previous unlock attempts.

A website may be provided where a user enters in his/her credit card number, pays a fee, and a new card is programmed and sent to the user. The new card may include a display to display a portion of the users credit/debit card number in a static form upon entry of an appropriate PIC. Such a card may also include one or more magnetic emulation circuits to transmit the information to a reader. Such a card may or may not, for example, include a portion of a magnetic stripe. For example, three tracks of magnetic stripe data may be communicated via three different emulation circuits, more than three different emulation circuits, one emulation circuits (e.g., tracks communicated serially to all read-heads), or one or more tracks may be represented by magnetic stripe(s) while one or more other tracks may be represented by a magnetic emulation circuit. A track of data may also be partially represented by a magnetic emulation circuit and partially represented by a magnetic stripe.

An LED may blink in a pattern to provide a number of functionalities. For example, an LED may blink to denote that a particular action is occurring (e.g., a magnetic emulator is ON). An LED may blink to communicate information to a card or other device (e.g., the video camera of a mobile telephone).

Figure 9:
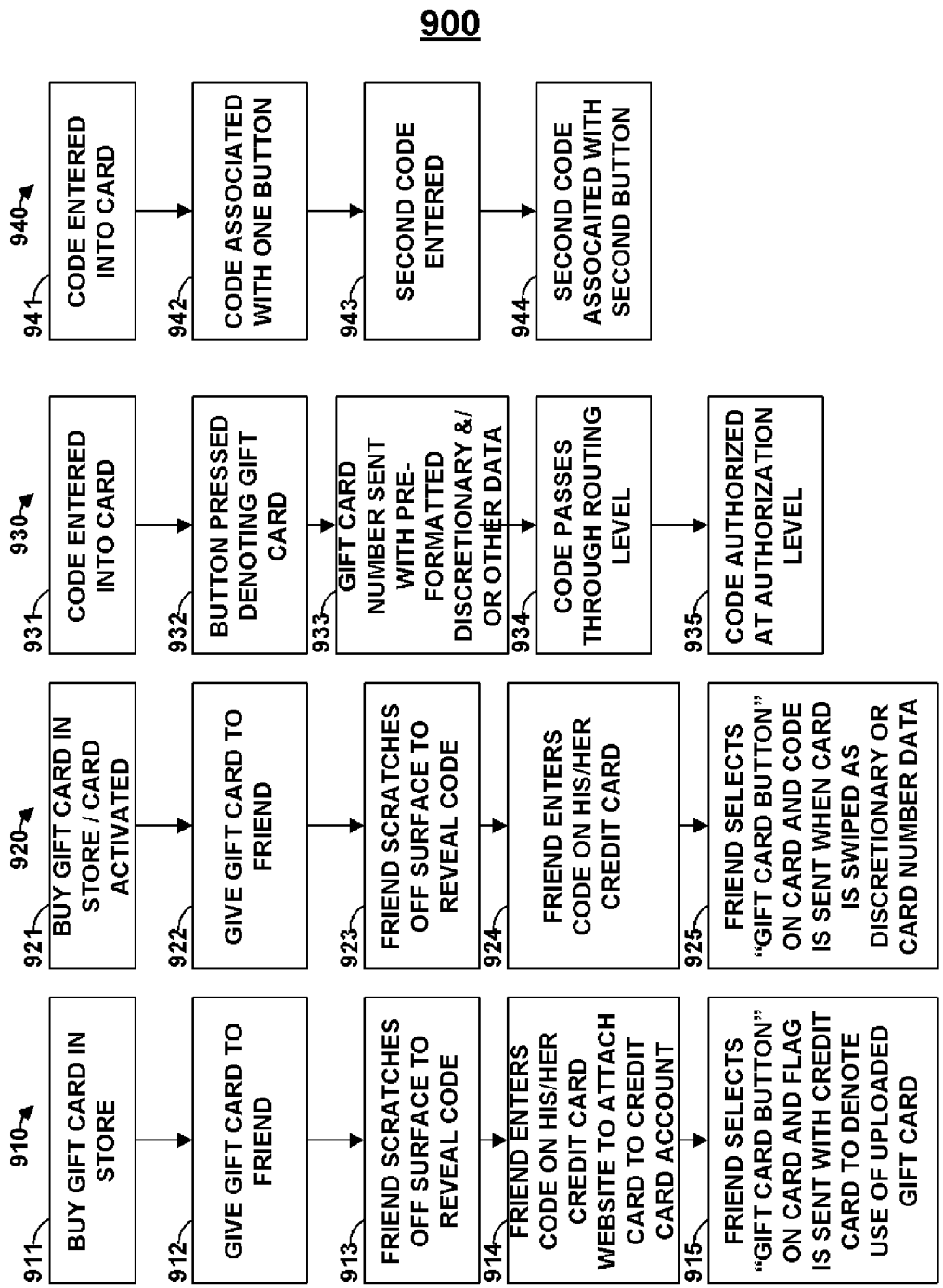
FIG. 9 is an illustration of process flow charts constructed in accordance with the principles of the present invention.

FIG. 9 shows process flow charts 900. Flow chart 910 may be included that includes step 911, in which a gift card is purchased in a store. Step 912 may then occur, in which the gift card is transferred to a friend or relative. Step 913 may ensue, in which the friend or relative scratches off a surface of the card to reveal a code. Step 914 may occur, in which the friend or relative may enter the code on a website associated with his/her card to attach the card to his/her payment card account. Step 915 may be included in which the friend or relative presses a button on his/her payment card and a flag is sent with the payment card information (e.g., payment card number, name, discretionary data) to denote that an uploaded card is desired to be utilized. As such, a server may utilize the gift card number linked to the payment card instead of, for example, the credit card number.

Flow chart 920 may be included. Step 921 may be included in flow chart 920, in which a gift card is purchased in a store and activated as a result of the card being purchased. Step 922 may occur, in which the gift card is given to a friend or relative. Step 923 may then occur, in which the friend or relative scratches off the surface of the card to reveal a code. Step 924 may be included in which the friend or relative enters the code on his/her payment card. Step 925 may be included in which the friend presses a button such that the code is transmitted when the card is utilized by a reader (e.g., a magnetic stripe reader) as discretionary or other data (e.g., credit card number data).

Flow chart 930 may be included. Step 931 may be included in flow chart 930, in which a code is entered into a card (or other device). A button may be pressed denoting use of a gift card function in step 932. Step 933 may be utilized such that the gift card data may be sent with pre-formatted discretionary and/or other data. Step 934 may be included such that the code passes through a routing server. Persons skilled in the art will appreciate that particular digits (e.g., the first six digits)

of a gift card number may be utilized by a server as a routing address. Step 935 may be included, for example, such that the code is authorized at an authentication server such that the gift card may be verified and utilized to pay for a purchase.

Flow chart 940 may be included. Step 941 may be included in flow chart 940 such that a code is entered into a card. Step 942 may be included such that the code is associated with one or more buttons on a card. Step 943 may be utilized such that a second code is entered into a card. Step 944 may be utilized such that a second code is associated with one or more second button. Accordingly, for example, one gift card may be entered and associated with one button while another gift card may be entered and associated with another button.

Persons skilled in the art will appreciate that a variety of accounting functions may be performed by a card (or other device). For example, buttons may be provided that are associated with different accounting categories (e.g., food, hotel, entertainment, gas, other). A user may press a button before a purchase in order to add information into the discretionary data associated with, for example, a category. Such information may be communicated to a magnetic emulator, encoder, RFID, and IC chip. Such information may be stripped out at a server and forwarded to a different server. Such a different server, may, for example, utilize such discretionary data to add information associated with the categories to a user's online bill statement for a particular payment card. Thus, for example, a user may select a business credit card button on a card and then a travel button. In doing so, for example, the user's business credit card number may be communicated to a magnetic stripe read-head (along with any associated information) as well as discretionary data representative of the purchase being for travel. Accordingly, a business person may save time in creating an expense report as information is communicated at time of purchase through a payment infrastructure at the demand of the user.

Figure 10:
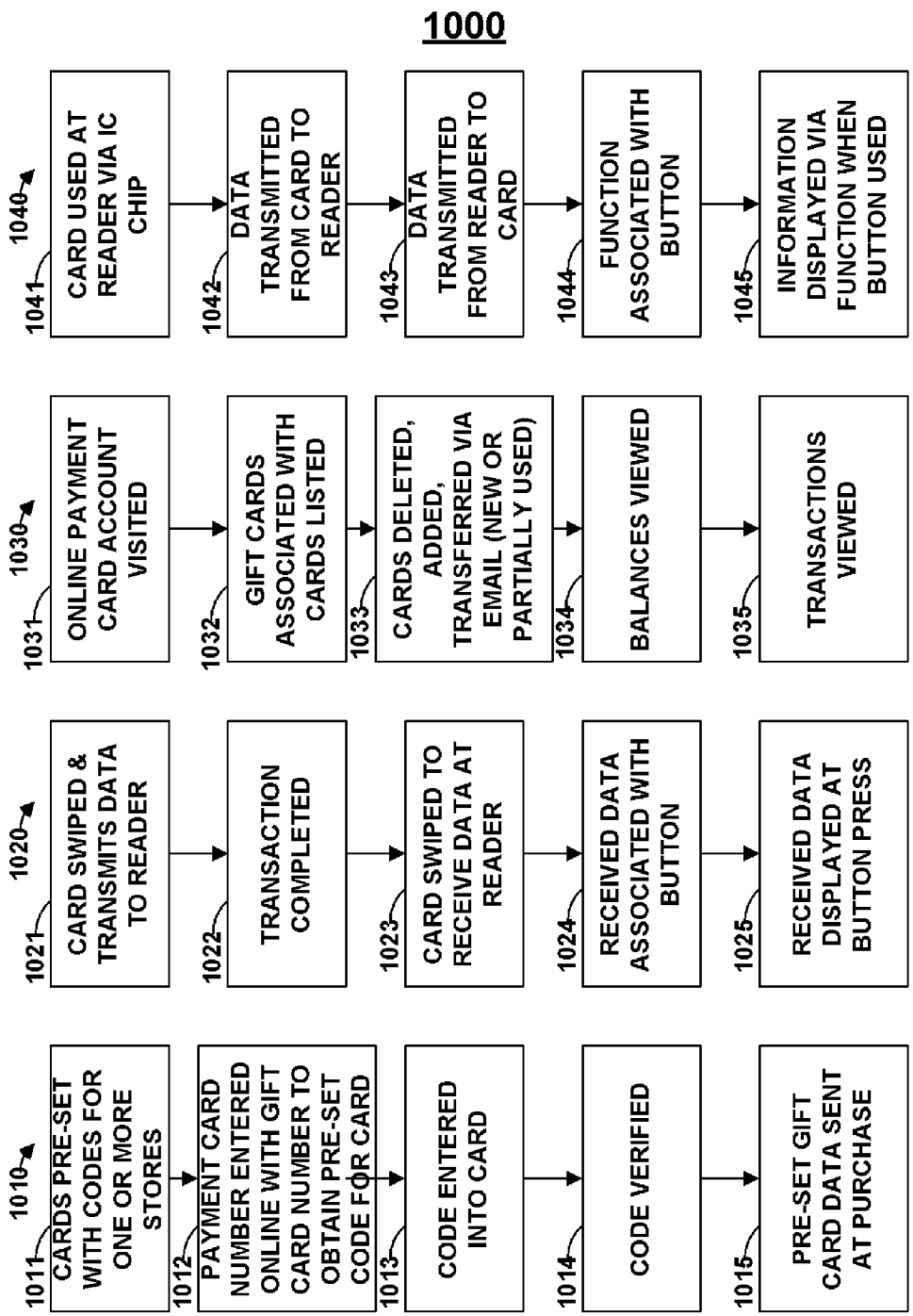
FIG. 10 is an illustration of process flow charts constructed in accordance with the principles of the present invention.

FIG. 10 may include process flow charts 1000. Flow chart 1010 may be included. Step 1011 may be included, in which a card is pre-set with codes for one or more stores. Step 1012 may occur, in which a payment card number is entered online with a gift card number to obtain a pre-set code for a store for a particular card (or for any card). Such a code may be entered into a card in step 1113. The code may be verified in step 1014 and pre-set gift card data may be sent at purchase in step 1015 (e.g., via a magnetic emulator, encoder, IC chip, or RFID).

Flow chart 1020 may be included that may include step 1021, in which a card may be swiped to transmit data to a reader (e.g., a magnetic stripe reader). Step 1022 may occur in which a transaction is completed. Step 1023 may then ensue, in which a card is swiped through the reader (e.g., a magnetic stripe reader) to receive data from the reader. The received data may be, at least in part, associated with a button in step 1024. Such received data may be displayed, at least in part, when the associated button is pressed in step 1025.

Flow chart 1030 may be included. Step 1031 may be included, in which an online card account may be be visited by a user. Step 1032 may be included in which gift cards associated with the card account may be listed with the card. Additional cards may be listed such as, for example, additional credit, debit, check, or pre-paid cards. Cards may be added, deleted, or transferred electronically (e.g., via mail) in step 1133. A balance may be viewed for one or more cards in step 1134. Transactions associated with cards may be viewed in step 1135.

Flow chart 1040 may be included. Card may be used at a reader via an IC chip in step 1041. Step 1042 may be included in which data may be transmitted from a card to a reader. Step 1043 may occur in which data may be transmitted from a reader to a card. A function may be associated with one or more buttons in step 1044. Information may be displayed via a function when the associated button is pressed in, for example, step 1045.

Figure 11:
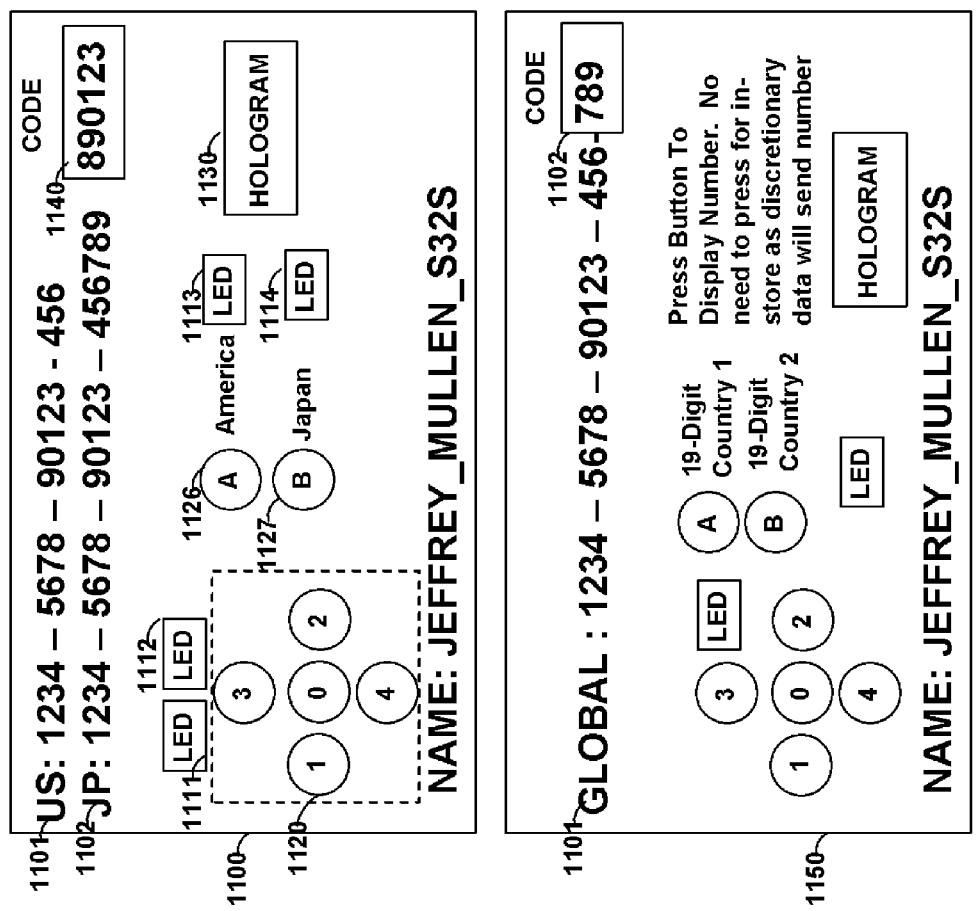
FIG. 11 is an illustration of cards constructed in accordance with the principles of the present invention.

FIG. 11 shows card 1100 that may include, for example, button array 1120, light sources 1111-1114, hologram 1130, permanent information 1101 and 1102, display 1140, and buttons 1126 and 1127. Permanent information 1101 and 1102 may be, for example, printed and/or embossed. Permanent information 1101 may correspond to, for example, the card number for one territory while permanent information 1102 may include information for another territory. Display 1140 may include, for example, a code that may change based on transaction (via read-head detectors), button-press, or time. The code displayed on display 1140 may be associated with buttons 1126 and 1127 such that different codes are provided depending on the button that is pressed. A code may be different lengths. Persons skilled in the art will appreciate, for example, that one payment card may include a card number of one length (e.g., 15 digits) and a code of one length (e.g., 4 digits) while another payment card may include a card number of a different length (e.g., 16 digits) and a code of a different length (e.g., 3 digits). Light source 1111 may activate in certain circumstances while light source 1112 may activate in different circumstances. Each light source may be able to emit different colors of light. Each light source may, for example, emit a different color of light. For example, light source 1111 may emit GREEN while light source 1112 may emit RED. Accordingly, for example, an appropriate PAC may result in light source 1111 emitting GREEN while light source 1112 emits RED. Light source 1113 may be utilized to emit light after button 1126 is pressed so that a user can see that a button is active. Similarly, button 1127 may be utilized to emit light after button 1127 is pressed.

Card 1150 may be provided. Global number 1101 may be displayed permanently (or via a display). Display 1102 may be utilized to display information. For example, display 1102 may be utilized to display a code or a portion of a payment card number. Persons skilled in the art will appreciate that different territories may be have different lengths of different types of data (e.g., different lengths of payment card numbers). Accordingly, a user may be assigned numbers in each territory with overlapping digits (e.g., global portions). For example, a sixteen digit number for one territory may be the same as the first sixteen digits of a nineteen digit number in another territory. The remaining digits for that territory may be displayed, for example, on display 1102. Accordingly, for example, the card may, upon entry of an appropriate PAC default to not showing any information on a display and, upon sensing of a read-head, sending the default payment information through one or more magnetic emulators and/or encoders (or RFID or IC chip). Upon the utilization of a button signifying a nineteen digit scheme for a different territory is utilized, the extra digit information may be displayed on display 1102 and the payment information for that territory may be communicated via a magnetic emulator, magnetic encoder, RFID, or IC chip. Persons skilled in the art will appreciate that pressing a button for a particular territory (or other payment information) may be utilized to send that payment information through a communications device such as a magnetic emulator. However, for example, another button may be utilized to cause a display to display the appropriate corresponding payment information. Accordingly, for example, a user may protect information from being visible read by others in particular situations (e.g., when a card is handed to a bartender for processing).

Figure 12:
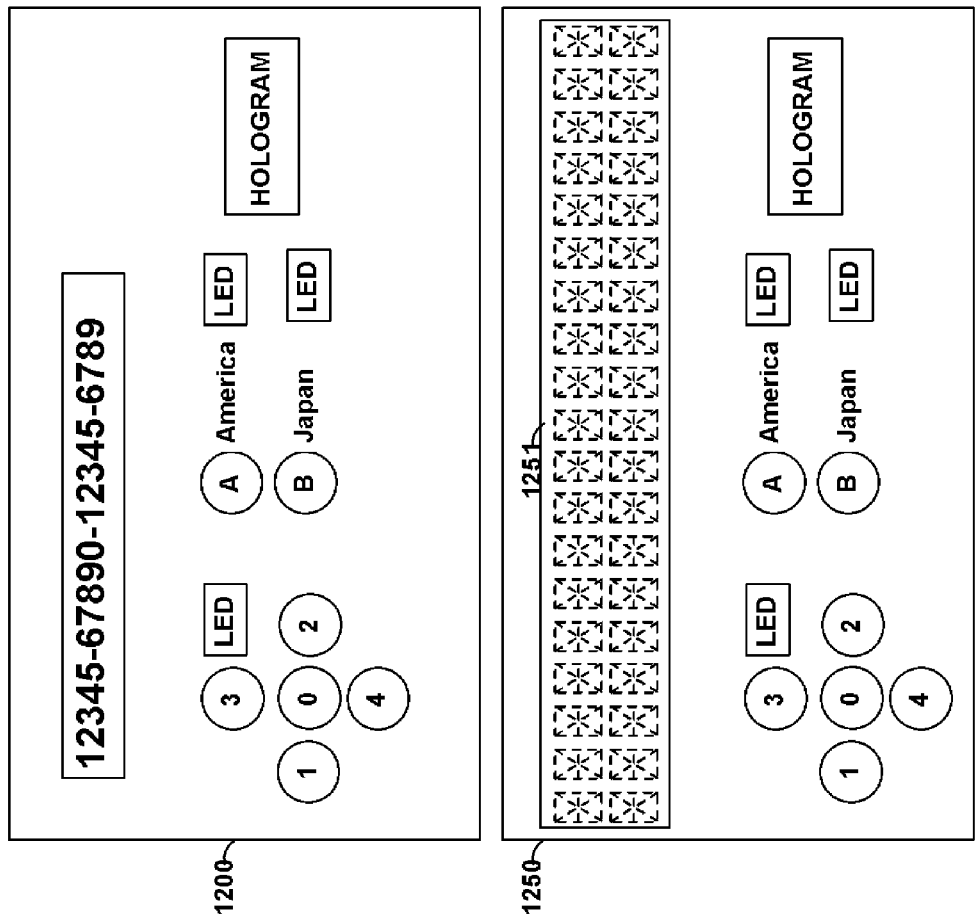
FIG. 12 is an illustration of cards constructed in accordance with the principles of the present invention.

FIG. 12 may include card 1200 in which a payment card number may be displayed on a display. Persons skilled in the art will appreciate that a variety of information may be displayed on a display such as, for example, battery life, time until a number expires (e.g., in a time-based encryption scheme), the number of numbers left (e.g., in a multiple-factor one-time-use scheme). Card 1250 may be provided that may include display 1251 that may include, for example 11-segment character displays. A card may include any type of display such as, for example, a 7-segment digit display. A display may be one, two, three or more lines of characters. A display may include pixels that may be controlled to display data. A color or two-tone (e.g., black and white) display may be utilized).

Figure 13:
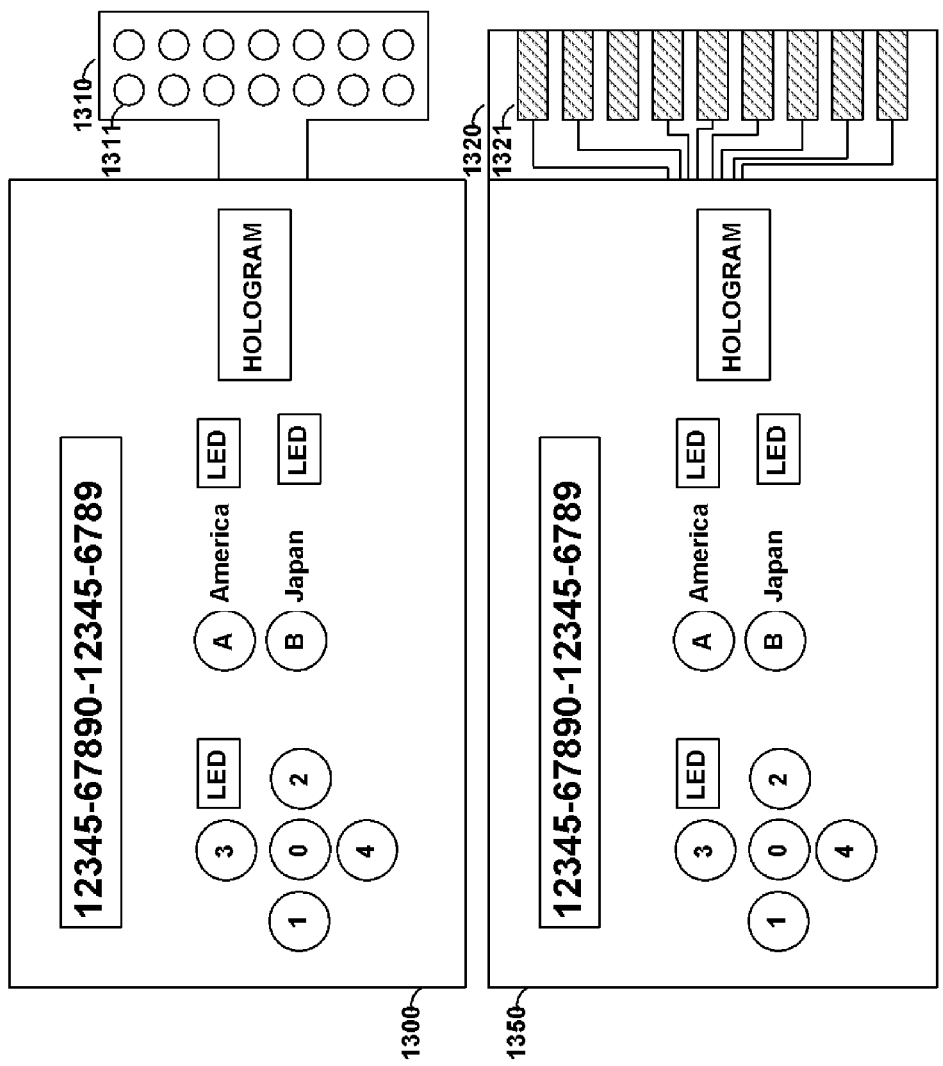
FIG. 13 is an illustration of cards constructed in accordance with the principles of the present invention.

FIG. 13 shows card 300 which may be manufactured and laminated (e.g., via a HOT, WARM, or COLD lamination process). A card may be printed on a circuit board, such as a flexible circuit board. Components (e.g., microprocessor) may be attached to the board (e.g., soldered via hot air). The card may be laminated. For example, the board may be placed into a mold and warm laminate may be injected into the mold. The mold may be removed such that a card is provided. Molding may take place, for example, on the sheet level and then cut into cards. Programming portion 1310 may be a portion of the board that was not laminated. The board may have, for example, multiple layers. Accordingly, portion 1310 may be utilized to program a processor, or other components, via contacts 1310. Contacts 1310 may take the form of, for example, rings such that a male-programming connector may couple each ring. Accordingly, a perpendicular connection may occur. After a card is programmed, for example, portion 1310 may be cut-off such that a card is provided. Card 1350 may be included with portion 1320 and contacts 1321. Contacts 1321 may couple via a parallel connection with a programmer. A microprocessor may be instructed to ignore or burn-out programming ports after programming. Additional laminate may be placed on the edge where the board is cut such that, for example, no contacts are exposed. Furthermore, a processor may be programmed through laminate using, for example, capacitive programming.

Figure 14:
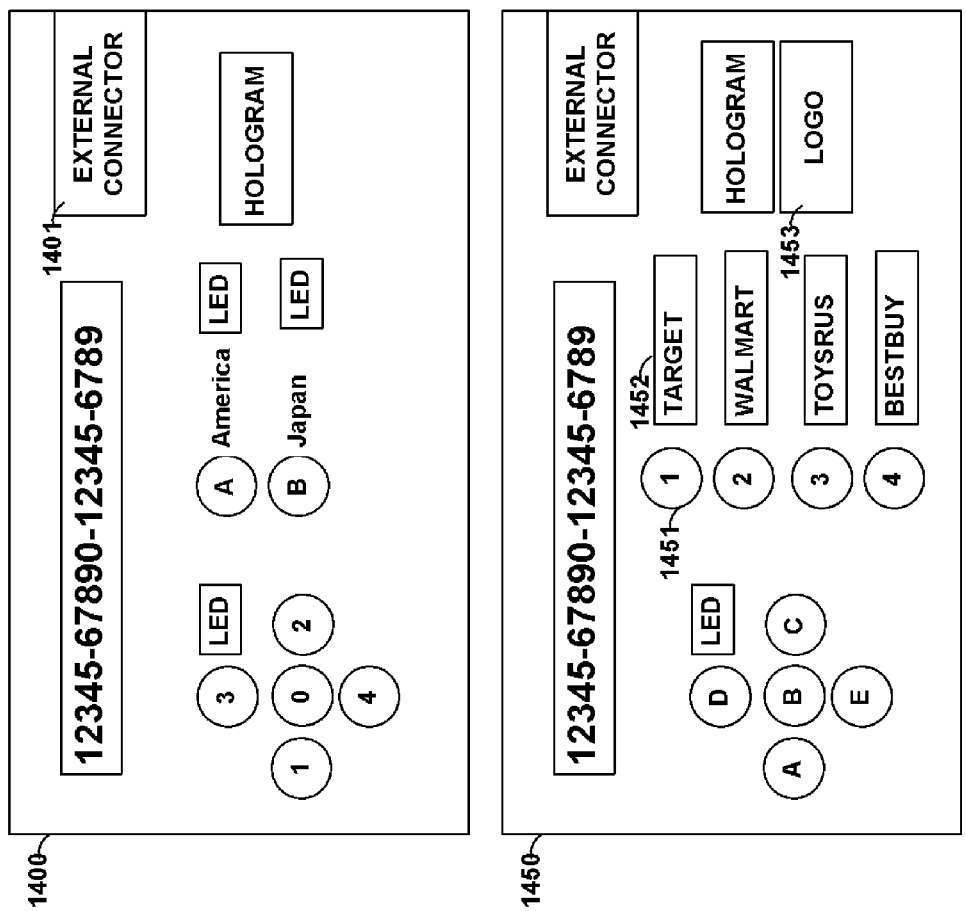
FIG. 14 is an illustration of cards constructed in accordance with the principles of the present invention.

FIG. 14 may include external connector 1401 which may be, for example, a USB connector. Such a USB connector may, for example, fold out from card 1400. Such a connector may be, for example, USB, USB 2.0, mini-USB, or USB 3.0. Other external connectors may be utilized. Data may be transferred to and from a card, or other device, utilizing external connector 1401.

Card 1450 may be provided. Card 1450 may include, for example, button 1451 and associated display 1452. A code may be entered using a button array to cause a processor to display a particular number, character set (e.g., name), logo, or other indicia on display 1452 upon the utilization of button 1451. Accordingly, for example, a user may load a gift card onto a card and may be provided with customized visual indicia such that a user may not forget what card is associated with what button. A user may select what button a card (e.g., gift card) may be associated with or the card may autonomously associate a card to the next available button. A card may have a pre-set number of cards that are provided to buttons on a one card per button basis or multiple cards may be associated per button (e.g., a single button press of a button provides one gift card while two button presses of a button in tandem provides a different gift card). Balances, gift card amounts, expiration dates, or other information may also be provided via a display. Other information may include a message from the gift card purchaser. A display may scroll data autonomously such that information that would extend beyond the display capabilities of a display may be displayed by the display without further user interaction. Accordingly, for example, a user may unlock a card by entering a particular PAC on a button array, the user may press a button to see the gift card associated with that button, the user may then select a different button and see a different gift card associated with that different button, the user may then swipe a card and a read-head detector may detect a swipe, the processor may then drive one or more magnetic emulators to communicate data to one or more magnetic stripe read-heads that causes that different credit card to be utilized. Persons skilled in the art will appreciate that codes may be utilized to, for example, load cards or denote a particular flag be sent with particular payment card information (e.g., default credit card information) such that processing servers may utilized gift cards linked to a card. Similarly, for example, a user may load a gift card into a card and the card may send information along with the payment card information (e.g., in discretionary fields) such that a processing server notes that a gift card was added to the card and links the gift card to the user's account. Accordingly, a user may, for example, receive a gift card, enter the card into his card (e.g., by entering a unique code for that gift card), use the credit card, and then go online to his payment card account and see that the loaded gift card is associated to his account. The user then may, for example, utilize the loaded gift card online from his/her payment card account.

Permanent logo 1453 may be provided on a card. A card may include logos of multiple credit card companies, banks, or other entities. A logo may be provided on a display (e.g., an electronic ink display). Different logos may be provided on a display and a particular button press may cause a different logo to be displayed. Different logos of different stores may be displayed depending on, for example, the gift card that is utilized at a particular time.

Figure 15:
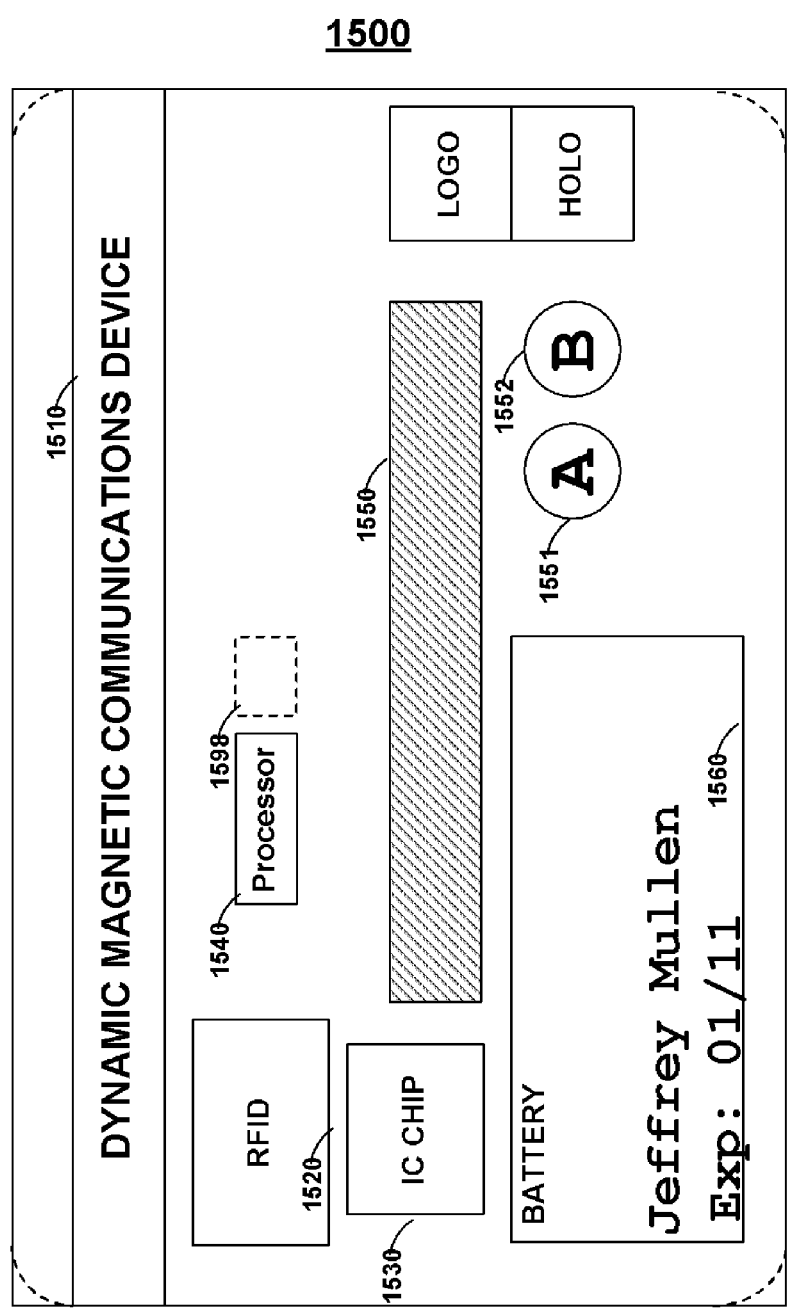
FIG. 15 is an illustration of a card constructed in accordance with the principles of the present invention.

FIG. 15 shows card 1500 that may include, for example, one or more IC chips 1530 (e.g., EMV chips), RFID antennas 1520, processors 1540, displays 1550, dynamic magnetic communications devices 1510 (e.g., magnetic encoders and/or magnetic emulators), batteries 1560, and buttons 1551 and 1552. Additional circuitry 1598 may be provided which may be, for example, one or more oscillators or emulator driving circuits. Persons skilled in the art will appreciate that button 1551 may, for example, be utilized by a user to select one encryption algorithm for a number displayed on display 1550 while button 1552 may be utilized by a user to select a different encryption algorithm. Persons skilled in the art will appreciate that the components of card 1500 may be provided on either surface of a card (e.g., a front or rear surface of the card) or inside of a card. A logo (e.g., of a card issuer) and logo may be provided on either surface of a card.

A button, such as button 1551, may be utilized, for example, to display a number. Such a number may be, for example, encrypted from a secure number based on time or use. For example, one-time use numbers (e.g., a payment number or code) may be retrieved from a list of numbers on memory each time button 1551 is pressed and displayed on display 1550. A processor may only go through each number once on a list. A registration process may be provided in which a user may be requested to enter in a sequence of numbers such that a remote server may validate the card and learn where in a sequence of a list a card currently resides. Numbers may be repeated on a list or may only occur once on a list. All of the numbers available by the length of the number may be utilized by the list or only a portion of the numbers available by the length of the number may be provided by the list. A secret number may be encrypted on a card and a verification server may also have knowledge of this secret number. Accordingly, the remote server may perform the same encryption function as the card on the secret number and verify that the resultant encrypted number is the same as the resultant encrypted number on a card. Alternatively, for example, the remote server may decrypt the received encrypted number to determine the authenticity of the encrypted number and validate an activity (e.g., validate a security access request or a purchase transaction).

Persons skilled in the art will appreciate, for example, that a card may include an IC chip (e.g., EMV chip), RFID, and a dynamic magnetic communications device (e.g., a magnetic emulator or encoder). The same information may be communicated through, for example, any number of such devices (e.g., a dynamic magnetic communications device, RFID, and an EMV chip). A central processor may cause each device to communicate the information (in the same format or a different format). Each component may have its own processor or driving circuitry. Such individual processors or driving circuitry may be coupled to a central processor. An EMV chip may be utilized, for example, to provide control signals to other devices (e.g., circuitry driving a display as well as a dynamic magnetic communications device). Such an EMV chip may receive signals provided by one or more buttons to determine, for example, that a particular button, or sequence of buttons, was pressed by a user.

Persons skilled in the art will appreciate that a read-head housing may include, for example, multiple read-heads. A read-head detector may, more generally, detect a read-head housing and, in doing so, detect a read-head.

Figure 16:
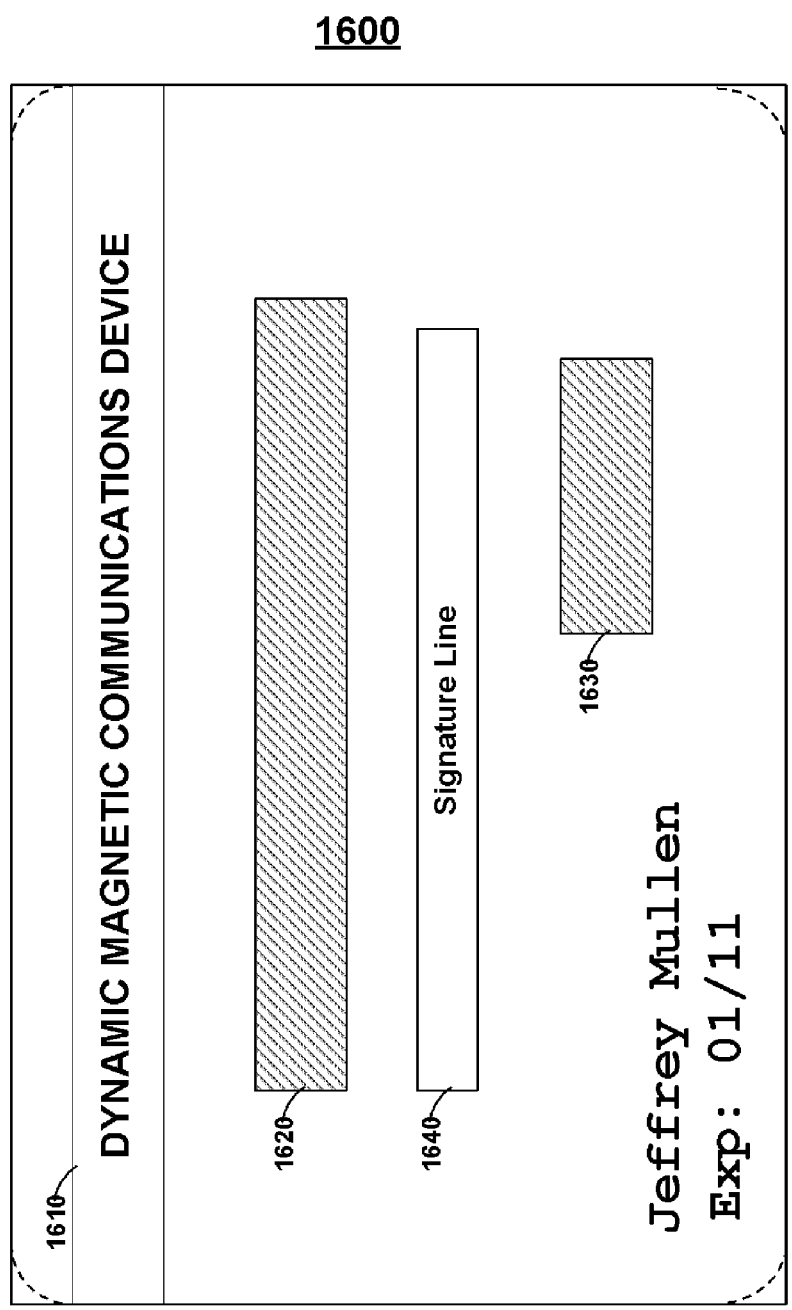
FIG. 16 is an illustration of a card constructed in accordance with the principles of the present invention.

FIG. 16 shows card 1600 that may include, for example, signature area 1640 that may include a material operable to receive marks from a pen (e.g., a signature). Card 1600 may also include, for example, displays 1620 and 1630. Display 1620 may, for example, display a payment number while display 1930 displays a security code (e.g., for online purchase authentication). Display 1620 as well as display 1630 may be utilized on the same side as, for example, dynamic magnetic communications device 1610.

Figure 17:
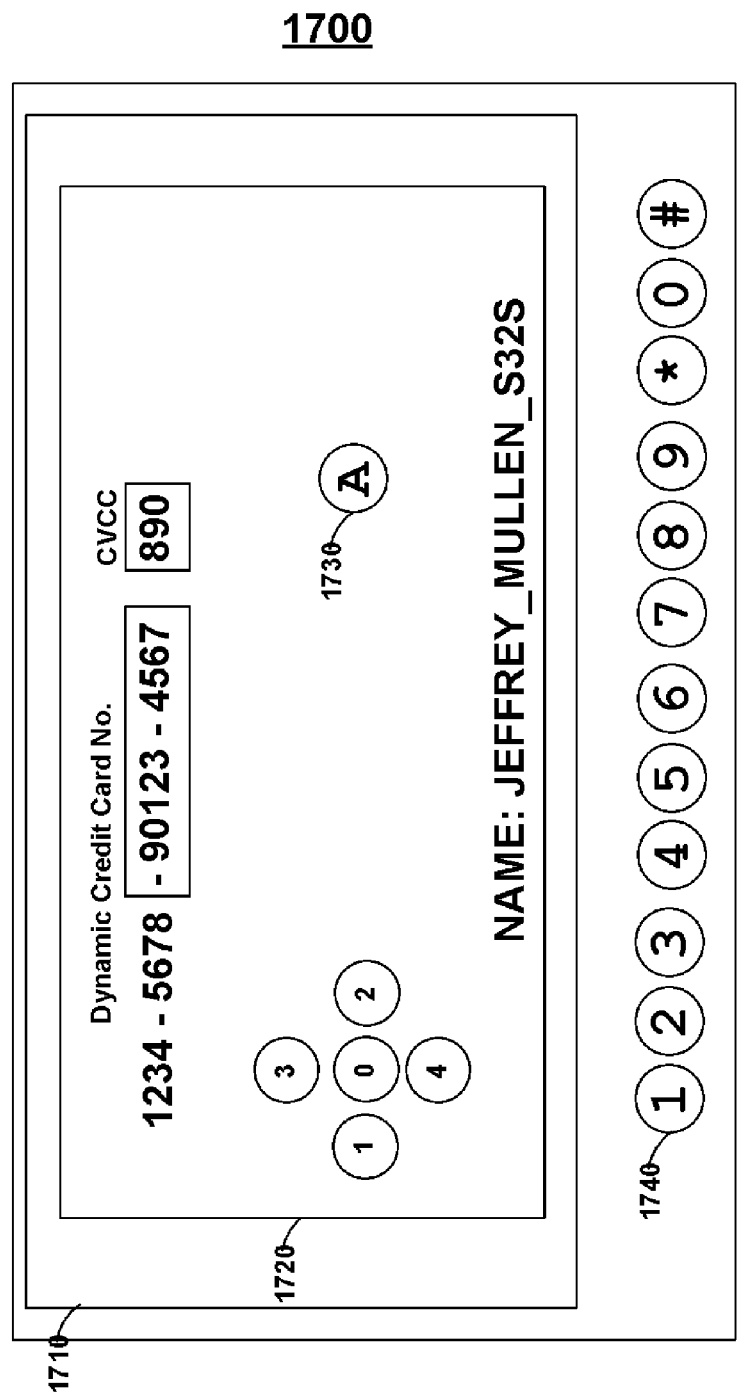
FIG. 17 is an illustration of a personal electronic device constructed in accordance with the principles of the present invention.

FIG. 17 shows personal electronic device 1700 which may be, for example, a portable telephonic device, portable media player, or any type of electronic device. Persons skilled in the art will appreciate that the functionality of a card may be provided on a personal device and displayed through a graphical user interface. Personal electronic device 1700 may include, for example, user inputs 1740 and display 1710. Virtual card 1720 may be displayed on display 1720. Display 1720 may be a touch-sensitive display such that, for example, virtual button 1230 may be provided on virtual card 1720. Persons skilled in the art will appreciate that cards may be provided as virtual cards and a user may interact with such virtual cards in order to provide a variety of functions. Personal electronic device 1700 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

A magnetic stripe reader may, for example, determine information on a magnetic stripe by detecting the frequency of changes in magnetic fields (e.g., flux transversals). A particular frequency of flux transversals may correlate to, for example, a particular information state (e.g., a logic "1" or a logic "0"). Accordingly, for example, a magnetic emulator may change the direction of an electromagnetic field at particular frequencies in order to communicate a different state of information (e.g., a logic "1" or a logic "0").

Persons skilled in the art will appreciate that a magnetic emulator may electromagnetically communicate information serially by changing the magnitude of an electromagnetic field with respect to time. As such, for example, a current in a single direction may be provided through a magnetic emulator in order for that magnetic emulator to generate an electromagnetic field of a single direction and a particular magnitude. The current may then be removed from the magnetic emulator such that, for example, the electromagnetic field is removed. The creation of a presence of an electromagnetic field, and the removal of that electromagnetic field, may be utilized to communicate information to, for example, a magnetic stripe reader. A magnetic stripe reader may be configured to read, for example, the change in flux versus time and may associate an increase in an electromagnetic field (e.g., creation of a field) as one flux transversal and a decrease (e.g., removal of a field) as another transversal. In doing so, for example, driving circuitry (not shown) may be provided which, in turn, controls when current is provided to a magnetic emulator. The timing of magnetic flux transversals, as determined by a magnetic stripe reader, may be utilized by that reader to determine whether a logic one ("1") or logic zero ("0") was communicated. Accordingly, a driving circuit may change the frequency of when current is supplied and removed from a magnetic emulator in order to communicate a logic one ("1") or a logic zero ("0").

A driving circuit may, for example, change the direction of current supplied to a magnetic emulator to increase the amount of change in an electromagnetic field magnitude for a period of time. In doing so, for example, a magnetic stripe reader may more easily be able to discern overall changes in an electromagnetic field and, as such, may more easily be able to discern information. As such, for example, a driving circuit may increase the magnitude of an electromagnetic field by providing negative current, decrease the amount of negative current until no current is provided and provide an increasing positive current in order to provide a large swing in the magnitude of an electromagnetic field. Similarly, a driving circuit may switch from providing one amount of negative current (or positive current) to one amount of positive current (or negative current).

Persons skilled in the art will appreciate that a string of a particular bit of data (e.g., a string of logic zeros "0s") may be communicated before as well as after information is communicated through a magnetic emulator. A magnetic stripe reader may utilize such data, for example, to determine base timing information such that the magnetic stripe reader has a timing reference that the reader can utilize to assist in determining timing changes of perceived flux transversals. Accordingly, for example, a magnetic emulator may send data at different overall frequencies and a magnetic stripe reader may be able to reconfigure itself to receive data at such overall frequencies. Information may be encoded using, for example, Frequency/Double Frequency (F2F) encoding such that magnetic stripe readers may perform, F2F decoding.

A processor may control one or more emulators by, for example, controlling the direction of the current supplied through one or more segments of an emulator. By changing the direction of current through a region, for example, the direction of an electromagnetic field may be changed. Similarly, a processor may control one or more emulators by, for example, controlling the change in magnitude of current supplied through one or more segments of an emulator. As such, for example, a processor may increase the magnitude of current as well as decrease the magnitude of current supplied through an emulator. A processor may control the timing of such increases and decreases in current such that a magnetic emulator may, for example, communicate F2F encoded information.

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:

1. A graphical user interface displayed on a device comprising:
   a virtual button operable to link a merchant gift card to a credit card number, wherein a remote server is operable to recognize said merchant gift card is associated with a purchase and utilize said merchant gift card for said purchase.

2. The graphical user interface of claim 1, further comprising indicia of a merchant associated with said merchant gift card when said virtual button is pressed.

3. The graphical user interface of claim 1, further comprising indicia of a merchant and a dollar amount associated with said merchant gift card when said virtual button is pressed.

4. The graphical user interface of claim 1, further comprising indicia of a merchant, a dollar amount and an expiration date associated with said merchant gift card when said virtual button is pressed.

5. The graphical user interface of claim 1, further comprising a delete function associated with said link when said merchant gift card is utilized.

6. The graphical user interface of claim 1, further comprising indicia associated with a battery of said device.

7. The graphical user interface of claim 1, further comprising a second virtual button operable to link a second merchant gift card to said payment card number.

8. A device, comprising:
   a display for displaying a graphical user interface, said graphical user interface comprising a virtual button operable to link a merchant gift card to a credit card number, wherein a remote server is operable to recognize said merchant gift card is associated with a purchase and utilize said merchant gift card for said purchase.

9. The device of claim 8, wherein said graphical user interface further comprises indicia of a merchant associated with said merchant gift card when said virtual button is pressed.

10. The device of claim 8, wherein said graphical user interface further comprises indicia of a merchant and a dollar amount associated with said merchant gift card when said virtual button is pressed.

11. The device of claim 8, wherein said graphical user interface further comprises indicia of a merchant, a dollar amount and an expiration date associated with said merchant gift card when said virtual button is pressed.

12. The device of claim 8, wherein said graphical user interface further comprises a delete function associated with said link when said merchant gift card is utilized.

13. The device of claim 8, wherein said graphical user interface further comprises indicia associated with a battery of said device.

14. The device of claim 8, wherein said graphical user interface further comprises a second virtual button operable to link a second merchant gift card to said payment card number.

15. The device of claim 8, further comprising a battery.

16. The device of claim 8, further comprising a battery and a processor.

17. The device of claim 8, further comprising a battery, a processor and an IC chip.

18. The device of claim 8, wherein said display is a bi-stable display.

19. The device of claim 8, wherein said display is a non bi-stable display.

20. The device of claim 8, further comprising a dynamic magnetic communications device.

* * * * *